US010301310B2

(12) United States Patent
Reddington et al.

(10) Patent No.: US 10,301,310 B2
(45) Date of Patent: May 28, 2019

(54) COSMIC QUENCHERS

(71) Applicant: BIOSEARCH TECHNOLOGIES, INC., Petaluma, CA (US)

(72) Inventors: Mark Reddington, San Francisco, CA (US); Ronald M. Cook, Novato, CA (US); Ben Ayer, Petaluma, CA (US)

(73) Assignee: BIOSEARCH TECHNOLOGIES, INC., Petaluma, CA (US)

( * ) Notice: Subject to any disclaimer, the term of this patent is extended or adjusted under 35 U.S.C. 154(b) by 56 days.

(21) Appl. No.: 15/309,311

(22) PCT Filed: May 11, 2015

(86) PCT No.: PCT/US2015/030097
§ 371 (c)(1),
(2) Date: Nov. 7, 2016

(87) PCT Pub. No.: WO2015/172134
PCT Pub. Date: Nov. 12, 2015

(65) Prior Publication Data
US 2017/0114058 A1  Apr. 27, 2017

Related U.S. Application Data

(60) Provisional application No. 61/990,913, filed on May 9, 2014.

(51) Int. Cl.
| | |
|---|---|
| *C07H 17/02* | (2006.01) |
| *C07H 21/00* | (2006.01) |
| *C07D 455/04* | (2006.01) |
| *C07D 471/06* | (2006.01) |
| *C07F 9/6561* | (2006.01) |
| *C12Q 1/6818* | (2018.01) |

(52) U.S. Cl.
CPC .......... *C07D 471/06* (2013.01); *C07D 455/04* (2013.01); *C07F 9/6561* (2013.01); *C07H 17/02* (2013.01); *C07H 21/00* (2013.01); *C12Q 1/6818* (2013.01)

(58) Field of Classification Search
CPC .................................................. C07D 471/06
See application file for complete search history.

(56) References Cited

U.S. PATENT DOCUMENTS

| | | | |
|---|---|---|---|
| 3,996,345 A | 12/1976 | Ullman et al. | |
| 4,351,760 A | 9/1982 | Khanna et al. | |
| 4,391,904 A | 7/1983 | Litman et al. | |
| 4,683,195 A | 7/1987 | Mullis et al. | |
| 4,683,202 A | 7/1987 | Mullis et al. | |
| 4,739,044 A | 4/1988 | Stabinsky et al. | |
| 4,757,141 A | 7/1988 | Fung et al. | |
| 4,997,928 A | 3/1991 | Hobbs et al. | |
| 5,231,191 A | 7/1993 | Woo et al. | |
| 5,989,823 A | 11/1999 | Jayasena et al. | |
| 7,879,986 B2 | 2/2011 | Berry et al. | |
| 2005/0170363 A1 | 8/2005 | Reddington et al. | |
| 2005/0214833 A1 | 9/2005 | Carter et al. | |
| 2005/0272088 A1 | 12/2005 | Cook et al. | |
| 2007/0059752 A1 | 3/2007 | Cook et al. | |
| 2009/0259030 A1 | 10/2009 | Cook et al. | |
| 2010/0143901 A1* | 6/2010 | Newton | C12Q 1/6848 435/5 |
| 2011/0178280 A1 | 7/2011 | Cook et al. | |
| 2011/0282041 A1 | 11/2011 | Cook et al. | |

FOREIGN PATENT DOCUMENTS

| | | |
|---|---|---|
| KR | 2014-0023755 A | 2/2014 |
| WO | WO 1992/007864 | 5/1992 |
| WO | WO 1997/045539 | 12/1997 |

OTHER PUBLICATIONS

Lovell et al. "FRET Quenching of Photosensitizer Singlet Oxygen Generation" J. Phys. Chem. B, 2009, vol. 113, pp. 3203-3211.*
Adams, et al., J. Am. Chem. Soc. 105: 661-663 (1983).
Agrawal, S. et al., Tetrahedron Lett. 28:3539-3542 (1987).
Agrawal et al., Tetrahedron Letters, 31:1543-1546 (1990).
Berge et al., Journal of Pharmaceutical Science, 66: 1 19 (1977).
Bouizar et al., Eur. J. Biochem., 155: 141-147 (1986).
Browning et al., J. Immunol., 143: 1859-1867 (1989).
Cardullo et al., Proc. Natl. Acad. Sci. USA 85: 8790-8794 (1988).
Chow, et al., Nucl. Acids Res. 9: 2807-2817 (1981).
Compton, J., Nature, 350:91-92 (1991).
Cooper, J.P., et al., Biochemistry, 29:9261-9268 (1990).
Crea, et al., Nucl. Acids Res. 8: 2331-2348 (1980).
Daubendiek, et al., Nature Biotechnology, 15:273-277 (1997).
Debouck, C., et al., in supplement to Nature Genetics, 21:48-50 (1999).
Dexter, D.L., J. of Chemical Physics 21: 836-850 (1953).
Froehler, B., Nucleic Acids Res. 14:5399-5467 (1986).
Froehler, B., Tetrahedron Lett. 27:5575-5578 (1986).
Froehler et al., Nucleosides and Nucleotides 6:287-291 (1987).
Froehler et al. Nucleic Acids Res. 16:4831-4839 (1988).
Gait, et al., Nucl. Acids Res. 10: 6243-6254 (1982).
Gao, et al., Tetrahedron Lett. 32: 5477-5480 (1991).
Gibson, E.M., et al., Genome Methods, 6:995-1001 (1996).
Giesendorf, B.A.J., et al., Clinical Chemistry, 44:482-486 (1998).
Giusti et al., PCR Methods and Applications, 2: 223-227 (1993).
Gupta et al., Nucleic Acids Research, 19: 3019 (1991).
Heid et al., Genome Res. 6: 986-994 (1996).
Higuchi et al., Bio/Technology 10: 413-417 (1992).
Hochstrasser et al., Biophysical Chemistry 45: 133-141 (1992).
Holland, P.M., et al., Proc Natl. Acad. Sci USA, 88:7276-7289 (1991).
Joshi et al., J. Biol. Chem., 265: 14518-14525 (1990).

(Continued)

*Primary Examiner* — Joseph R Kosack
(74) *Attorney, Agent, or Firm* — Morgan, Lewis & Bockius LLP; Jeffry S. Mann

(57) ABSTRACT

The present invention provides quenchers of excited state energy, probes and other conjugates comprising these quenchers, and methods of their use.

32 Claims, 5 Drawing Sheets

(56) References Cited

OTHER PUBLICATIONS

Jung et al., Biochem. Biophys. Acta, 761: 152-162 (1983).
Kostrikis et al. Science 279:1228-1229 (1998).
Koster et al., Tetrahedron Lett. 24: 747-750 (1983).
Lee et al., BioTechniques 27: 342-349 (1999).
Lee, L.G., et al., Nucleic Acids Research., 21:3761-3766 (1993).
Lemaltre et al., Proc Natl Acad Sci. 84:648-652 (1987).
Lemaltre et al., Nucleosides and Nucleotides, 6:311-315 (1987).
Lizardi, P.M., et al., Nature Genetics, 19:225-232 (1998).
Lyamichev, V., et al., Nature Biotechnology, 17:292 (1999).
Matsuo, T., Biochemica et Biophysica Acta, 1379:178-184 (1998).
McCollum, et al., Tetrahedron Lett. 32: 4069-4072 (1991).
Nazarenko, I.A., et al., Nucleic Acids Research, 25:2516-2521 (1997).
Nelson et al., Nucleic Acids Research, 17: 7187-7194 (1989).
Park et al., J. Biol, Chem., 261: 205-210 (1986).
Piatek, A.S., et al., Nature Biotechnology, 16:359-363 (1998).
Reese, C. B. et al., Tetrahedron Lett. 26:2245-2248 (1985).
Rehman, F.N., et al., Nucleic Acids Research, 27:649-655 (1999).
Schofield, P., et al., Appl. Environ. Microbiology, 63:1143-1147 (1997).
Selvin, P., Methods in Enzymology 246: 300-334 (1995).
Sproat et al., Nucleic Acids Research, 15: 4837 (1987).
Steinberg, I. Ann. Rev. Biochem., 40: 83-114 (1971).
Stryer, L. Ann. Rev. Biochem., 47: 819-846 (1978).
Tyagi et al., Nature Biotechnology 14:303-308 (1996).
Tyagi et al. Nature Biotechnology 16: 49-53 (1998).
Uehara, H., et al., Biotechniques, 26:552-558 (1999).
Vamosi, G., et al., Biophysical Journal, 71:972-994 (1996).
Walker, G., et al., Nucleic Acids Res., 20:1691-1696 (1992).
Walker G.T., et al., Clinical Chemistry, 42:9-13 (1996).
Wang et al., Tetrahedron Letters 31: 6493-6496 (1990).
Wang et al., Anal. Chem. 67: 1197-1203 (1995).
Whitcombe, et al., Nature Biotechnology, 17:804-807 (1999).
Wittwer, C.T., et al., Biotechniques, 22:176-181 (1997).
Wittwer, C.T., et al., Biotechniques, 22:130-138 (1997).
Zarling et al., J. Immunol., 124: 913-920 (1980).
Zuckermann et al., Nucleic Acids Research, 15: 5305-5321 (1987).

\* cited by examiner

COSMIC QUENCHERS

CROSS-REFERENCE TO RELATED APPLICATIONS

This application claims under 35 USC 119(e) the benefit of U.S. Provisional Application No. 61/990,913, filed May 9, 2014, which is incorporated herein by reference in its entirety for all purposes.

SUMMARY OF THE INVENTION

The present invention provides quenchers of excited state energy, probes and other conjugates comprising these quenchers, and methods of their use. Other objects, advantages and aspects of the present invention will be apparent from the detailed description below.

BRIEF DESCRIPTION OF THE DRAWINGS

FIG. 5A shows the fluorescence intensity for the Quasar 670-Cosmic Quencher, Quasar 670-BHQ2, Quasar 670-BBQ, Quasar 705-Cosmic Quencher, and Quasar 705-BHQ2 probes in a nuclease digestion assay. FIG. 5B shows signal-to-noise ratios for the Quasar 670-Cosmic Quencher, Quasar 670-BHQ2, Quasar 670-BBQ, Quasar 705-Cosmic Quencher, and Quasar 705-BHQ2 probes in a nuclease digestion assay.

DETAILED DESCRIPTION OF THE INVENTION

Abbreviations

Figure 1:
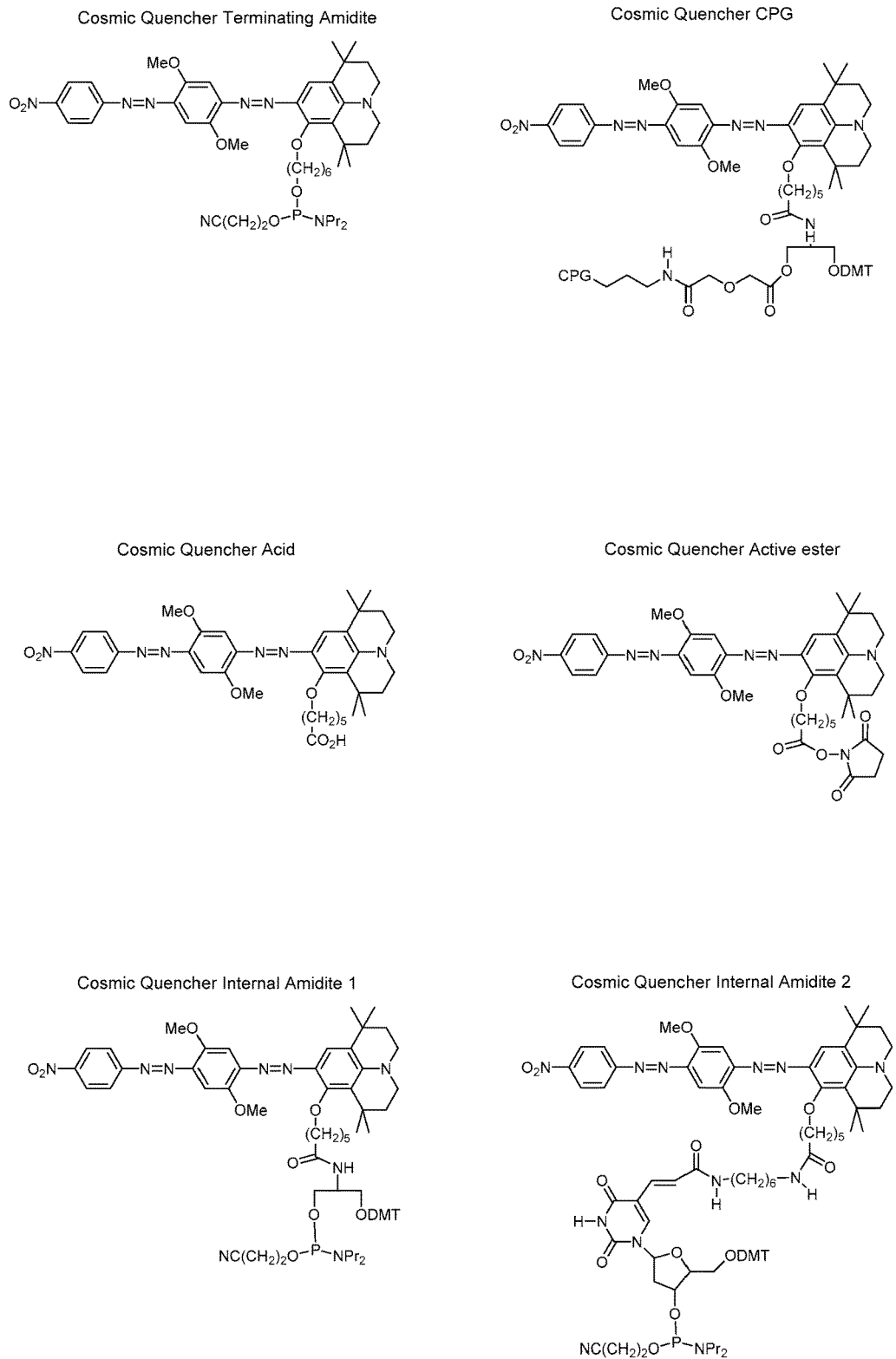
FIG. 1 shows exemplary compounds of the invention.

"BHQ," as used herein, refers generally to dark quenchers including one or more diazo bond and specifically to "Black Hole Quenchers™." Exemplary BHQ's are described in U.S. Pat. No. 7,019,129. "FET," as used herein, refers to "Fluorescence Energy Transfer." "FRET," as used herein, refers to "Fluorescence Resonance Energy Transfer." These terms are used herein to refer to both radiative and non-radiative energy transfer processes. For example, processes in which a photon is emitted and those involving long range electron transfer are included within these terms. Throughout this specification, both of these phenomena are subsumed under the general term "donor-acceptor energy transfer." "SNP" refers to "Single Nucleotide Polymorphism."

Definitions

The following definitions are broadly applicable to each of the embodiments of the present invention set forth hereinbelow. Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Molecular biological techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference). The nomenclature used herein and the laboratory procedures in analytical chemistry, and organic synthesis are those well known and commonly employed in the art. Standard techniques, or modifications thereof, are used for chemical syntheses and chemical analyses.

The term "alkyl," by itself or as part of another substituent, means, unless otherwise stated, a straight- or branched-chain, or cyclic hydrocarbon radical, or combination thereof, which may be fully saturated, mono- or polyunsaturated and can include mono-, di-, tri- and tetra-valent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, also optionally include those derivatives of alkyl defined in more detail below, such as "heteroalkyl." Alkyl groups that are limited to hydrocarbon groups are termed "homoalkyl". The term "alkyl", as used herein refers to alkyl, alkenyl and alkynyl moieties, each of which can be mono-, di- or polyvalent species as appropriate to satisfy valence requirements. Alkyl groups are optionally substituted, e.g., with one or more groups referred to herein as an "alkyl group substituent."

The term "alkylene" by itself or as part of another substituent means a divalent radical derived from an alkyl moiety, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. For alkylene and heteroalkylene linker groups, it is optional that no orientation of the linker group is implied by the direction in which the formula of the linker group is written. For example, the formula —C(O)$_2$R'— represents —C(O)$_2$R'— and, optionally, —R'C(O)$_2$—. A "lower alkyl" or "lower alkylene" is a shorter chain alkyl or alkylene group, generally having eight, seven, six, five or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight- or branched-chain, or cyclic alkyl radical consisting of the stated number of carbon atoms and at least one heteroatom selected from the group consisting of B, O, N, Si and S, wherein the heteroatom may optionally be oxidized and the nitrogen atom may optionally be quaternized. The heteroatom(s) may be placed at any internal position of the heteroalkyl group or at a terminus of the chain, e.g., the position through which the alkyl group is attached to the remainder of the molecule. Examples of "heteroalkyl" groups include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Two or more heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent refers to a substituted or unsubstituted divalent heteroalkyl radical, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like).

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings, one or more of which is optionally a cycloalkyl or heterocycloalkyl), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of "aryl group substituents" described below.

For brevity, the term "aryl" when used in combination with other terms (e.g., aryloxy, arylthioxy, arylalkyl) optionally includes both homoaryl and heteroaryl rings as defined above. Thus, the term "arylalkyl" optionally includes those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R"' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" includes groups with carbon atoms bound to groups other than hydrogen, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Exemplary alkyl group substituents include those groups referred to herein as "reactive functional groups" and "linkage sites." In various embodiments, the alkyl group substituent is a phosphorus-containing moiety, e.g., a phosphodiester or a phosphodiester modification such as those described herein.

Similar to the substituents described for the alkyl radical, substituents for the aryl and heteroaryl groups are generically referred to as "aryl group substituents." Exemplary substituents are selected from the list of alkyl group substituents and others, for example: halogen, —OR', =O, =NR', =N—OR', —NR'R", —SR', —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R"' and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R''' and R"" groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_{16}$)alkyl. Exemplary aryl group substituents include those groups referred to herein as "reactive functional groups" and "linkage sites."

As used herein, the term "heteroatom" includes oxygen (O), nitrogen (N), sulfur (S) and silicon (Si).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocyclyl groups. R can also refer to alkyl group substituents and aryl group substituents.

The term "salt(s)" includes salts of the compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate, and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts. Hydrates of the salts are also included.

As used herein, "nucleic acid" means nucleosides, nucleotides and oligonucleotides, e.g., DNA, RNA, whether single-stranded, double-stranded, or in more highly aggregated hybridization motifs, and any chemical modifications thereof. Modifications include, but are not limited to, those providing chemical groups that incorporate additional charge, polarizability, hydrogen bonding, electrostatic interaction, and reactivity to the nucleic acid ligand nucleobases or to the nucleic acid ligand as a whole. Such modifications include, but are not limited to, phosphodiester group modifications (e.g., phosphorothioates, methylphosphonates), sugar modifications, 5-position pyrimidine modifications, 8-position purine modifications, modifications at exocyclic amines, substitution with non-standard or non-natural nucleobases such as 4-thiouridine, 5-bromo or 5-iodo-uracil; backbone modifications such as peptide nucleic acids (PNAs), glycol nucleic acids (GNAs), morpholinos; methylations such as 2'-O-methyl nucleosides, 5-methyl-2'-deoxycytidine; unusual base-pairing combinations such as the isobases, isocytidine and isoguanidine and the like. A "nucleomonomer" refers to a single nucleic acid unit, which can be a nucleoside, nucleotide or a modification thereof.

"Nucleobase" as used herein includes those moieties which contain not only the known purine and pyrimidine heterocycles and the invention pyrimidines, but also heterocycle analogs and tautomers thereof. Purines include adenine and guanine, and exemplary purine analogs include 8-oxo-N$^6$-methyladenine and 7-deazaxanthine. Pyrimidines include thymine, uracil and cytosine, and their analogs such as 5-methylcytosine, 5-methyluracil and 4,4-ethanocytosine. This term also encompasses non-natural nucleobases. Representative non-natural nucleobases include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

In various embodiments, the inventive compounds include pyrimidines derivatized at the 5-position. The derivatives are 1-alkenyl-, 1-alkynyl-, heteroaromatic- and 1-alkynyl-heteroaromatic modifications. "1-Alkenyl" means an olefinically-unsaturated (double bond containing) acyclic group. "1-Alkynyl" means an acetylenically-unsaturated (triple bond containing) acylic group As used herein, "nucleoside" means a subset of nucleic acid in which a nucleobase is covalently attached to a sugar or sugar analog and which optionally includes a phosphite, phosphoramidite or phosphine. The term nucleoside includes ribonucleosides, deoxyribonucleosides, or any other nucleoside which is an N-glycoside or C-glycoside of a nucleobase. The stereochemistry of the sugar carbons can be other than that of D-ribose. Nucleosides also include those species which contain modifications of the sugar moiety, for example, wherein one or more of the hydroxyl groups are replaced with a halogen, a heteroatom, an aliphatic groups, or are functionalized as ethers, amines, thiols, and the like. The pentose moiety can be replaced by a hexose or an alternate structure such as a cyclopentane ring, a 6-member morpholino ring and the like. Nucleosides as defined herein also include a nucleobase linked to an amino acid and/or an amino acid analog having a free carboxyl group and/or a free amino group and/or protected forms thereof. Nucleosides also optionally include one or more nucleobase modification, e.g., modified with a fluorocarbyl, alkenyl or alkynyl moiety. A nucleoside including a phosphodiester or phosphodiester modification, is referred to herein as a nucleotide. Nucleosides as defined herein are also intended to include a nucleobase linked to an amino acid and/or an amino acid analog having a free carboxyl group and/or a free amino group and/or protected forms thereof.

"Sugar modification," as used herein, means any pentose or hexose moiety other than 2'-deoxyribose. Modified sugars include, for example, D-ribose, 2'-O-alkyl, 2'-amino, 2'-halo functionalized pentoses, hexoses and the like. Exemplary sugar modifications include those sugars in which one or more of the hydroxyl groups is replaced with a halogen, a heteroatom, an alkyl moiety, or are functionalized as ethers, esters, and the like. The pentose moiety can be replaced by a hexose or an alternate structure such as a cyclopentane ring, a 6-member morpholino ring and the like. Sugars having a stereochemistry other than that of a D-ribose are also included.

"Phosphodiester group modification" means any analog of the native phosphodiester group that covalently couples adjacent nucleomonomers. Substitute linkages include phosphodiester analogs, e.g. such as phosphorothioate and methylphosphonate, and nonphosphorus containing linkages, e.g. such as acetals and amides.

Nucleic acid modification also include 3', 5', and base modifications such as labeling with a quencher (e.g., a BHQ), a fluorophore, intercalator, minor groove binder, a fluorocarbon, a stabilizing group or another moiety. In various embodiments, the modification or label is covalently conjugated to the oligomer through a linker group.

Oligomers are defined herein as two or more nucleomonomers covalently coupled to each other by a phosphodiesester or modified phosphodiester moiety. Thus, an oligomer can have as few as two nucleomonomers (a dimer), and have essentially no upper limit of nucleomonomers. Oligomers can be binding competent and, thus, can base pair with cognate single-stranded or double-stranded (or higher order aggregation) nucleic acid sequences. Oligomers are also useful as synthons for longer oligomers as described herein. Oligomers can also contain abasic sites and pseudonucleosides. In various embodiments, the oligomers of the invention are functionalized. The moieties functionalizing the oligomers are discussed below. In describing certain embodiments the term "oligomer" is used interchangeably to refer to the nucleic acid sequence of the oligomer, the modified nucleic acid sequence providing a probe of the invention or the modified nucleic acid sequence providing a solid support of the invention.

"Peptide" refers to an oligomer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

A "solid support" is a solid material having a surface for attachment of molecules, compounds, cells, or other entities, or to which surface such species are attached. The surface of a solid support can be flat or otherwise configured. A solid support can be porous or non-porous. A solid support can be a chip or array that comprises a surface, and that may comprise glass, silicon, nylon, polymers, plastics, ceramics, or metals. A solid support can also be a membrane, such as a nylon, nitrocellulose, or polymeric membrane, or a plate or dish and can be comprised of glass, ceramics, metals, or plastics, such as, for example, a 96-well plate made of, for example, polystyrene, polypropylene, polycarbonate, or polyallomer. A solid support can also be a bead or particle of any shape, and is preferably spherical or nearly spherical, and preferably a bead or particle has a diameter or maximum width of 1 millimeter or less, more preferably of between 0.1 to 100 microns. Such particles or beads can be comprised of any suitable material, e.g., glass or ceramics, and/or one or more polymers, such as, for example, nylon, polytetrafluoroethylene, TEFLON™, polystyrene, polyacrylamide, sepaharose, agarose, cellulose, cellulose derivatives, or dextran, and/or can comprise metals, particularly paramagnetic metals, such as iron.

Supports for solid phase synthesis are known in the art and include, but are not limited to, high cross-linker polystyrene (McCollum, et al., *Tetrahedron Lett.* 32: 4069-4072 (1991), polystyrene/PEG copolymer (Gao, et al., *Tetrahedron Lett.* 32: 5477-5480 (1991), silica gel (Chow, et al., *Nucl. Acids Res.* 9: 2807-2817 (1981)), polyamide bonded silica gel (Gait, et al., *Nucl. Acids Res.* 10: 6243-6254 (1982)), cellulose (Crea, et al., *Nucl. Acids Res.* 8: 2331-2348 (1980)), and controlled pore glass (CPG) (Koster, et al., *Tetrahedron Lett.* 24: 747-750 (1983). An exemplary solid support is CPG beads. CPG beads can be derivatized for the attachment of a nucleomonor or oligomer in a variety of ways. For example, CPG beads can be treated with 3-aminopropyltriethoxysilane to add an amino propyl linker handle for the attachment of oligonucleotide analogue monomers or dimers (Koster, et al., *Tetrahedron Lett.* 24: 747-750 (1983), or, preferably, a long-chain alkylamine group, most preferably including a terminal nucleoside, can be attached to CPG (Adams, et al., *J. Am. Chem. Soc.* 105: 661-663 (1983)). Supports for oligonucleotide synthesis or peptide synthesis, for example dT-LCAA-CPG (Applied Biosystems), are commercially available.

An "intercalator" refers to a planar aromatic or heteroaromatic moiety that is capable of partial insertion and stacking between adjacent nucleobases. These moieties may be small molecules or part of a larger entity, such as a protein. Non-limiting examples of intercalators include acridines, anthracenes, anthracyclines, anthracyclinone, methylene blue, indole, anthraquinone, quinoline, isoquinoline, dihydroquinones, tetracyclines, psoralens, coumarins, ethidium halides, ethidium homodimers, homodimeric oxazole yellow (YOYO), thiazole orange (TOTO), dynemicins, 1,10-phenanthroline-copper, calcheamicin, porphyrins, distamycins, netropcins, and viologens.

A "minor groove binder" refers to a moiety typically having a molecular weight of approximately 150 to approximately 2000 Daltons. The moiety binds in a non-intercalating manner into the minor groove of double stranded (or higher order aggregation) DNA, RNA or hybrids thereof, preferably, with an association constant greater than approximately $10^3$ $M^{-1}$. Minor groove binding compounds have widely varying chemical structures, however, exemplary minor groove binders have a crescent shape three dimensional structure. Exemplar include certain naturally occurring compounds such as netropsin, distamycin and lexitropsin, mithramycin, chromomycin $A_3$, olivomycin, anthramycin, sibiromycin, as well as further related antibiotics and synthetic derivatives. Certain bisquarternary ammonium heterocyclic compounds, diarylamidines such as pentamidine, stilbamidine and berenil, CC-1065 and related pyrroloindole and indole polypeptides, Hoechst 33258, 4'-6-diamidino-2-phenylindole (DAPI) as well as a number of oligopeptides consisting of naturally occurring or synthetic amino acids are minor groove binder compounds. Exemplary minor groove binders are described in U.S. Pat. No. 6,084,102. This type of binding can be detected by well established spectrophotometric methods, such as ultraviolet (u.v.) and nuclear magnetic resonance (NMR) spectroscopy and also by gel electrophoresis. Shifts in u.v. spectra upon binding of a minor groove binder molecule, and NMR spectroscopy utilizing the "Nuclear Overhauser" (NOSEY) effect are particularly well known and useful techniques for this purpose. Gel electrophoresis detects binding of a minor groove binder to double stranded DNA or fragment thereof, because upon such binding the mobility of the double stranded DNA changes.

The minor groove binder is typically attached to the oligomer or solid support through a linker comprising a chain about 20, about 15 atoms, about 10 or about 5 atoms.

Intercalating moieties or agents are readily distinguished from minor groove binders on the basis that the intercalating agents are flat aromatic (preferably polycyclic) molecules versus the "crescent shape" or analogous geometry of the minor groove binders. An experimental distinction can also be made by NMR spectroscopy utilizing the Nuclear Overhauser effect.

The term "linker" or "L", as used herein, refers to a single covalent bond ("zero-order") or a series of stable covalent bonds incorporating 1-30 nonhydrogen atoms selected from the group consisting of C, N, O, S, Si and P that covalently link together the components of the compounds of the invention, e.g., linking a solid support to a stabilizing agent, a quencher, a nucleomonomer or oligomer of the invention; or linking a quencher or stabilizing moiety to a nucleobase in an amidite of the invention. Exemplary linkers include 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 non-hydrogen atoms. Unless otherwise specified, "linking," "linked," "linkage," "conjugating," "conjugated" and analogous terms relating to attachment refer to techniques utilizing and species incorporating linkers. Exemplary linkers include a linkage site as defined herein. Moreover, a linker is of use to attach an oligomer or nascent oligomer (during oligomer synthesis) to the solid support of the invention. Thus, the invention also provides an oligomer of the invention covalently attached to a solid support (e.g., a solid support of the invention) through a linker. The solid supports and oligomers of the invention optionally include a cleavable linker between two components of the solid support and oligomer (e.g., between the oligomer and the solid support, between the fluorophore and oligomer, between the quencher and oligomer, between the fluorophore and quencher, etc.). In various embodiments, the linker joining the solid support to the oligomer is a cleavable linker.

A "cleavable linker" is a linker that has one or more cleavable groups that may be broken by the result of a reaction or condition. An exemplary cleavable linker is located within $R^8$ of Formula I or II, serving to allow for the expedient separation of a synthesized oligomer of the invention from the solid support upon which it was synthesized. The term "cleavable group" refers to a moiety that allows for release of a component of the solid support or oligomer of the invention by cleaving a bond linking the released moiety to the remainder of the conjugate. Exemplary cleavage mechanisms of use both in preparing and using the oligomers and solid supports of the invention are enzymatically or otherwise chemically mediated.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, ortho-hydroxcinnamate esters, benzoin esters), and heat. Many cleaveable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989). Moreover a broad range of cleavable, bifunctional (both homo- and hetero-bifunctional) spacer arms are commercially available.

An exemplary cleavable group is cleavable by a reagent, e.g. sodium hydroxide, ammonia or other amine. In various embodiments the cleavable linker is readily cleaved at room temperature or under heat. In one embodiment, $R^8$ of Formula I or II comprises a cleavable linker that is cleaved by treatment with an amine, e.g., ammonia or an essentially anhydrous amine in an organic solvent.

A "linkage site," is a moiety that connects two or more components (e.g., functional component, solid support, oligonucleotide, or linker). This term refers to a covalent bond that is formed by reaction of complementary reaction partners, each of which has a functional group of complementary reactivity to that of its partner. Linkage sites in the solid support and oligomers of the invention are independently selected. Exemplary linkage sites include, but are not limited to S, SC(O)NH, HNC(O)S, SC(O)O, O, NH, NHC(O), (O)CNH and NHC(O)O, and OC(O)NH, $CH_2S$, $CH_2O$, $CH_2CH_2O$, $CH_2CH_2S$, $(CH_2)_oO$, $(CH_2)_oS$ or $(CH_2)_oY^x$-PEG wherein, $Y^x$ is S, NH, NHC(O), C(O)NH, NHC(O)O, OC(O)NH, or O and o is an integer from 1 to 50. In each of these exemplary linkage sites, NH can be $NR^L$ in which $R^L$ is substituted or unsubstituted alkyl or substituted or unsubstituted heteroalkyl. A linkage site can also be a phosphodiester group. In various embodiments, the linkage site is between a linker and a fluorophore, a linker and a quencher, a linker and a stabilizing moiety or a linker and a solid support. In an exemplary embodiment of the oligomers and solid support of the invention, each linkage site is different.

The term "fluorophore" as used herein refers to a moiety that is inherently fluorescent or demonstrates a change in fluorescence upon binding to a biological compound or metal ion, or metabolism by an enzyme, i.e., fluorogenic. Fluorophores may be substituted to alter the solubility, spectral properties or physical properties of the fluorophore. Numerous fluorophores are known to those skilled in the art and include, but are not limited to coumarins, acridines, furans, dansyls, cyanines, pyrenes, naphthalenes, benzofurans, quinolines, quinazolinones, indoles, benzazoles, borapolyazaindacenes, oxazines and xanthenes, with the latter including fluoresceins, rhodamines, rosamines and rhodols. These and other fluorophores of use in the invention are described in Haugland, MOLECULAR PROBES HANDBOOK OF FLUORESCENT PROBES AND RESEARCH CHEMICALS. Further useful fluorophores are described in commonly owned U.S. Patent Application Publication No. 2005/0214833 and 2005/0170363 and herein below.

As used herein, "quencher" refers to any fluorescence-modifying moiety of the invention that can attenuate at least partly the light emitted by a fluorophore. This attenuation is referred to herein as "quenching". Hence, in various embodiments, excitation of the fluorophore in the presence of the quenching group leads to an emission signal that is less intense than expected, or even completely absent. Quenching typically occurs through energy transfer between the excited fluorophore and the quenching group.

The fluorophore or quencher may include substituents enhancing a desirable property, e.g., solubility in water, cell permeability or an altered absorption and emission spectrum, relative to the "parent" compound in the absence of such substituent. As such the fluorophore or quencher of use in the invention include substituents that enhance a desirable property relative to an identical parent compound in the absence of the improving substituent.

A "functional component" is a generic term for a moiety in a compound of the invention having a structure selected from a quencher, a fluorophore or a stabilizing moiety (including, but not limited to, intercalators, minor groove binding moieties, nucleobases modified with a stabilizing moiety (e.g., alkynyl moieties, and fluoroalkyl moieties), and conformational stabilizing moieties, such as those described in commonly owned U.S. Patent Application Publication No. 2007/0059752).

The expression "amplification of polynucleotides" includes but is not limited to methods such as polymerase chain reaction (PCR), ligation amplification (or ligase chain reaction, LCR) and amplification methods based on the use of Q-beta replicase. These methods are well known and widely practiced in the art. See, e.g., U.S. Pat. Nos. 4,683,195 and 4,683,202 and Innis et al., 1990 (for PCR); and Wu et al., 1989a (for LCR). Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments has been described by Scharf (1986). The present invention provides oligomeric primers of use in amplification processes. Moreover, there is provided a solid support of use in synthesizing such primers. In addition to primers, the invention provides probes, and methods of using such probes, to detect, characterize and/or quantify the products of amplification: also provided are solid supports of use to synthesize these oligomeric probes.

The term "base-stacking perturbations" refers to any event that causes a perturbation in base-stacking such as, for example, a base-pair mismatch, a protein binding to its recognition site, or any other entities that form oligonucleotide adducts. Various probes of the invention are capable of detecting, characterizing and/or quantifying such base-stacking perturbations. Moreover, the invention provides solid supports of use in synthesizing probes capable of detecting, characterizing and/or quantifying such base-stacking perturbations.

The term "hybridized" refers to two nucleic acid strands associated with each other which may or may not be fully base-paired: generally, this term refers to an association including an oligomer of the invention whether bound to a solid support or in solution.

The term "denaturing" refers to the process by which strands of nucleic acid duplexes (or higher order aggregates) are no longer base-paired by hydrogen bonding and are separated into single-stranded molecules. Methods of denaturation are well known to those skilled in the art and include thermal denaturation and alkaline denaturation. This term generally refers to the dissociation of a probe of the invention from its target nucleic acid.

The term "mismatches" refers to nucleic acid nucleobases within hybridized nucleic acid duplexes (or higher order aggregates) which are not 100% complementary. A mismatch includes any incorrect pairing between the nucleobases of two nucleobases located on complementary strands of nucleic acid that are not the Watson-Crick base-pairs, e.g., A:T or G:C. The lack of total homology may be due to deletions, insertions, inversions, substitutions or frameshift mutations. In various embodiments, the oligomer of the invention includes a mismatch relative to its target nucleic acid, preferably allowing detection and/or characterization and/or quantification of the corresponding mismatch in its target. In certain embodiments, the mismatch is a single nucleotide mismatch.

As used herein, the term "polymorphism" refers to a sequence variation in a gene, and "mutation" refers to a sequence variation in a gene that is associated or believed to be associated with a phenotype. The term "gene" refers to a segment of the genome coding for a functional product protein control region. Polymorphic markers used in accordance with the present invention for subject identification may be located in coding or non-coding regions of the genome, and various probes of the invention are designed to hybridize to nucleic acid regions including these markers. The term "subject," as used herein refers to a subject providing a test sample from which target nucleic acids are obtained for the purpose of genetic testing. The oligomers of the invention are of use in detecting and/or characterizing and/or quantifying polymorphisms and mutations. Moreover, the solid supports of the invention are of use in synthesizing oligomers of use to detect and/or characterize and/or quantitate polymorphisms and mutations.

The term "probe" as used herein refers to nucleic acid oligomers prepared using a solid support or amidite of the invention. In various embodiments, the probes produce a detectable response upon interaction with a binding partner. The probes include at least one detectable moiety, or a pair of moieties that form an energy transfer pair detectable upon some change of state of the probe in response to its interaction with a binding partner. The present invention provides probes and amidites and solid supports of use to synthesize probes. Exemplary probes of the invention are of use to detect a polymorphism. In various embodiments, the polymorphism is a single nucleotide polymorphism (SNP).

The term "detectable response" as used herein refers to a change in or an occurrence of, a signal that is directly or indirectly detectable either by observation or by instrumentation and the presence of or, preferably, the magnitude of which is a function of the presence of a target binding partner for a probe in the test sample. Typically, the detectable response is an optical response from a fluorophore resulting in a change in the wavelength distribution patterns or intensity of absorbance or fluorescence or a change in light scatter, fluorescence quantum yield, fluorescence lifetime, fluorescence polarization, a shift in excitation or emission wavelength or a combination of the above parameters. The detectable change in a given spectral property is generally an increase or a decrease in fluorescence intensity. However, spectral changes that result in a shift in the wavelength of fluorescence emission or excitation are also useful. The change in fluorescence on ion binding is usually due to conformational or electronic changes in the indicator that may occur in either the excited or ground state of the fluorophore, due to changes in electron density at the ion binding site, due to quenching of fluorescence by the bound target metal ion, or due to any combination of these or other effects. Alternatively, the detectable response is an occurrence of a signal wherein the fluorophore is inherently fluorescent and does not produce a change in signal upon binding to a metal ion or biological compound. The present invention provides probes providing a detectable response and solid supports of use to synthesize such probes.

The term "carrier molecule" as used herein refers to any molecule to which a compound of the invention is attached. Representative carrier molecules include a protein (e.g., enzyme, antibody), glycoprotein, peptide, saccharide (e.g., mono-, oligo-, and poly-saccharides), hormone, receptor, antigen, substrate, metabolite, transition state analog, cofactor, inhibitor, drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism.

The symbol ∽, displayed perpendicular to a bond, indicates the point at which the displayed moiety is attached to the remainder of the molecule.

In some embodiments, the definition of terms used herein is according to IUPAC.

Cosmic Quenchers

In one aspect, the invention provides a compound (quencher) having a structure according to Formula I or II:

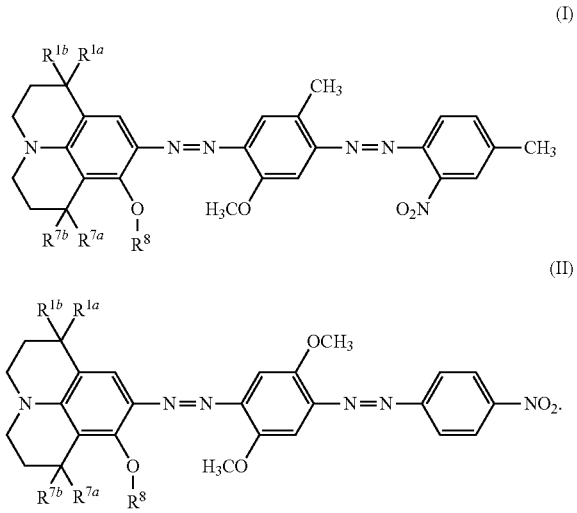

$R^{1a}$, $R^{1b}$, $R^{7a}$, and $R^{7b}$ are independently selected from H, substituted or unsubstituted alkyl, substituted or unsubstituted cycloalkyl, substituted or unsubstituted heteroalkyl, and substituted or unsubstituted heterocycloalkyl.

$R^{1a}$ and $R^{1b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl.

$R^{7a}$, and $R^{7b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl.

At least one of $R^{1a}$, $R^{1b}$, $R^{7a}$, and $R^{7b}$ is not H.

$R^8$ is selected from H,

$L^x$, $L^{xs}$, $R^s$, and $R^x$ are as defined herein.

Any of the combinations of $R^{1a}$, $R^{1b}$, $R^{7a}$, $R^{7b}$, and $R^8$ are encompassed by this disclosure and specifically provided by the invention.

In some embodiments, $R^{1a}$ and $R^{1b}$ are each H.

In some embodiments, $R^{1a}$ and $R^{1b}$ are independently selected from unsubstituted $C_1$, $C_2$, $C_3$, $C_4$, $C_5$, and $C_6$ alkyl.

In some embodiments, $R^{1a}$ and $R^{1b}$ are each methyl.

In some embodiments, $R^{7a}$ and $R^{7b}$ are each H.

In some embodiments, $R^{7a}$ and $R^{7b}$ are independently selected from unsubstituted $C_1$, $C_2$, $C_3$, $C_4$, $C_5$, and $C_6$ alkyl.

In some embodiments, $R^{7a}$ and $R^{7b}$ are each methyl.

In some embodiments, $R^{1a}$ and $R^{1b}$ are independently selected from unsubstituted $C_1$, $C_2$, $C_3$, $C_4$, $C_5$, and $C_6$ alkyl, and $R^{7a}$ and $R^{7b}$ are each H.

In some embodiments, $R^{1a}$ and $R^{1b}$ are each methyl, and $R^{7a}$ and $R^{7b}$ are each H.

In some embodiments, $R^{1a}$ and $R^{1b}$ are each H, and $R^{7a}$ and $R^{7b}$ are independently selected from unsubstituted $C_1$, $C_2$, $C_3$, $C_4$, $C_5$, and $C_6$ alkyl.

In some embodiments, $R^{1a}$ and $R^{1b}$ are each H, and $R^{7a}$ and $R^{7b}$ are each methyl.

In some embodiments, $R^{1a}$, $R^{1b}$, $R^{7a}$, and $R^{7b}$ are independently selected from unsubstituted $C_1$, $C_2$, $C_3$, $C_4$, $C_5$, and $C_6$ alkyl.

In some embodiments, $R^{1a}$, $R^{1b}$, $R^{7a}$, and $R^{7b}$ are each methyl.

In some embodiments, $L^x$ is selected from a bond, substituted or unsubstituted alkyl, substituted or unsubstituted cycloalkyl, substituted or unsubstituted heteroalkyl, and substituted or unsubstituted heterocycloalkyl.

In some embodiments, $L^x$ is selected from unsubstituted $C_1$, $C_2$, $C_3$, $C_4$, $C_5$, $C_6$, $C_7$, $C_8$, $C_9$, and $C_{10}$ alkyl.

In some embodiments, $L^{xs}$ is selected from substituted or unsubstituted alkyl, substituted or unsubstituted cycloalkyl, substituted or unsubstituted heteroalkyl, and substituted or unsubstituted heterocycloalkyl.

In some embodiments, $L^{xs}$ is substituted heteroalkyl.

In some embodiments, $R^s$ is selected from a protected or unprotected reactive functional group, a linkage site, and a solid support.

In some embodiments, $R^s$ is selected from —OH, —ODMT, and a linkage site covalently bound to a linker to a solid support.

"DMT" refers to 4,4'-dimethoxytrityl.

In some embodiments, the solid support is controlled pore glass (CPG).

In some embodiments, $R^x$ is selected from a protected or unprotected reactive functional group and a linkage site.

In some embodiments, $R^x$ is selected from a phosphoramidite, —OH, —ODMT, —COOH, an active ester (such as an N-Hydroxysuccinimide (NHS) ester), and —NH$_2$.

"DMT" refers to 4,4'-dimethoxytrityl.

In some embodiments, the linkage site is covalently bound to a member independently selected from a nucleoside, a linker to a nucleoside, a nucleotide, a linker to a nucleotide, an oligonucleotide, a linker to an oligonucleotide, a nucleic acid, a linker to a nucleic acid, a carrier molecule, a linker to a carrier molecule, a solid support, and a linker to a solid support.

In some embodiments, $R^x$ is a linkage site covalently bound to a linker to a nucleoside, wherein said nucleoside has the structure:

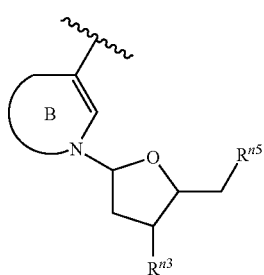

wherein the ring labeled B is a nucleobase;

$R^{n3}$ is —OH or a phosphoramidite; and $R^{n5}$ is —OH or -ODMT.

"DMT" refers to 4,4'-dimethoxytrityl.

In some embodiments, $R^8$ is selected from:

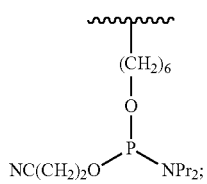

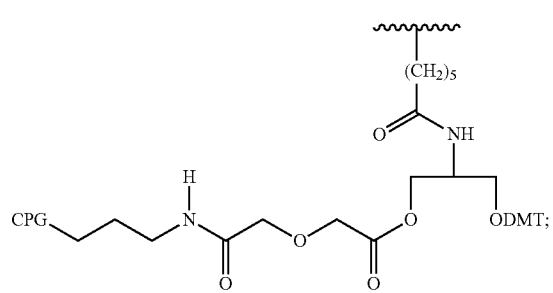

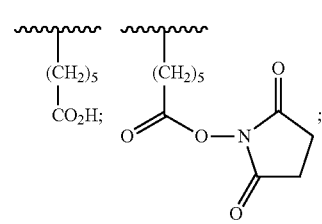

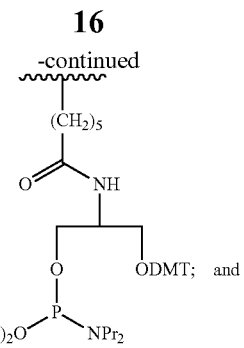

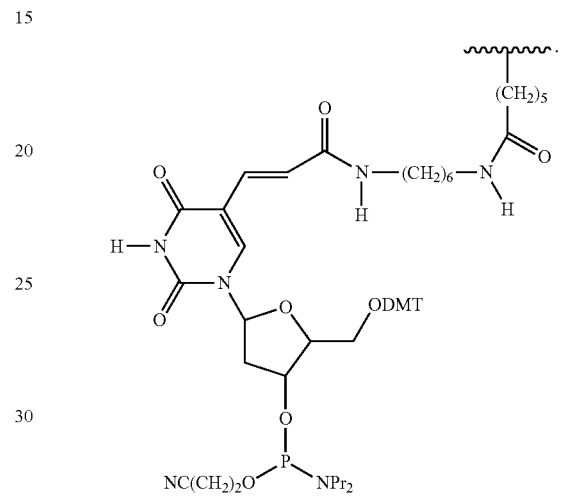

Monomers

In various embodiments, the invention provides monomeric nucleic acids of use in synthesizing oligomers with an internal modification. In a representative embodiment, the monomeric nucleic acid bears a quencher moiety. An exemplary monomeric nucleic acid according to this embodiment has the formula:

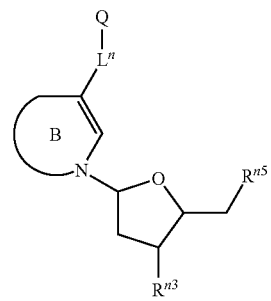

wherein Q is a quencher moiety;

$L^n$ is a linker;

the ring labeled B is a nucleobase;

$R^{n3}$ is —OH or a phosphoramidite; and $R^{n5}$ is —OH or -ODMT.

"DMT" refers to 4,4'-dimethoxytrityl.

In some embodiments, the quencher moiety (Q) has a structure according to Formula I or II:

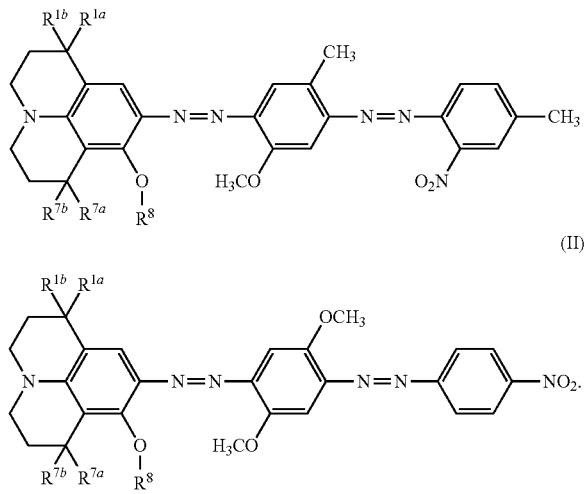

wherein $R^{1a}$, $R^{1b}$, $R^{7a}$, $R^{7b}$ and $R^8$ are as defined herein; and $R^8$ comprises a linkage site covalently bound to $L^n$.

In some embodiments, $L^n$ is selected from a bond, substituted or unsubstituted alkyl, substituted or unsubstituted cycloalkyl, substituted or unsubstituted heteroalkyl, and substituted or unsubstituted heterocycloalkyl.

Exemplary nucleobases include:

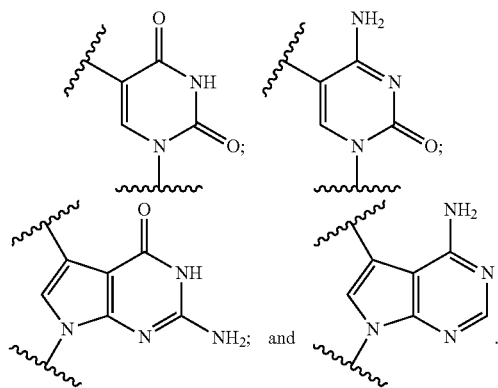

Oligomers

Also provided is a nucleic acid oligomer, e.g., a probe, prepared using a monomer of the invention and including the components of the monomer from which it is synthesized.

Exemplary oligomers include oligonucleotides, oligonucleosides, oligodeoxyribonucleotides (containing 2'-deoxy-D-ribose or modified forms thereof), i.e., DNA, oligoribonucleotides (containing D-ribose or modified forms thereof), i.e., RNA, and any other type of polynucleotide which is an N-glycoside or C-glycoside of a purine or pyrimidine nucleobase, or modified purine or pyrimidine nucleobase. Oligomer as used herein also includes compounds where adjacent nucleomonomers are linked via amide linkages as previously described (Nielsen et al., *Science* (1991) 254:1497-1500). Elements ordinarily found in oligomers, such as the furanose ring and/or the phosphodiester linkage can be replaced with any suitable functionally equivalent element. "Oligomer" is thus intended to include any structure that serves as a scaffold or support for the nucleobases wherein the scaffold permits binding to target nucleic acids in a sequence-dependent manner.

Exemplary groups linking nucleomonomers in an oligomer of the invention include (i) phosphodiester and phosphodiester modifications (phosphorothioate, methylphosphonate, etc), (ii) substitute linkages that contain a non-phosphorous isostere (formacetal, riboacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

The oligomers of the invention can be formed using modified and conventional nucleomonomers and synthesized using standard solid phase (or solution phase) oligomer synthesis techniques, which are now commercially available. In general, the oligomers can be synthesized by a method comprising the steps of: synthesizing a nucleomonomer or oligomer synthon having a protecting group and a nucleobase and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized.

The oligomers of the present invention can be of any length including those of greater than 40, 50 or 100 nucleomonomers. In various embodiments, oligomers contain 2-100 nucleomonomers. Lengths of greater than or equal to about 10 to 40 nucleomonomers are useful for therapeutic or diagnostic applications. Short oligomers containing 2, 3, 4 or 5 nucleomonomers are specifically included in the present invention and are useful, e.g., as synthons.

Oligomers having a randomized sequence and containing fewer than 20, fewer than 15 or fewer than 10 nucleomonomers are useful for primers, e.g., in cloning or amplification protocols that use random sequence primers, provided that the oligomer contains residues that can serve as a primer for polymerases or reverse transcriptases.

Oligomers can contain conventional phosphodiester linkages or can contain phosphodiester modification such as phosphoramidate linkages. These substitute linkages include, but are not limited to, embodiments wherein a moiety of the formula —O—P(O)(S)—O— ("phosphorothioate"), —O—P(S)(S)—O— ("phosphorodithioate"), —O—P(O)—(NR$^o_2$)—X—, —O—P(O)(R$^o$)—O—O—P(S)(R$^o$)—O— ("thionoalkylphosphonate"), —P(O)(OR$^P$)—X—, —O—C(O)—X—, or —O—C(O)(NR$^P_2$)—X—, wherein R$^o$ is H (or a salt) or alkyl (1-12C) and R$^P$ is alkyl (1-9C) and the linkage is joined to adjacent nucleomonomers through an —O— or —S— bonded to a carbon of the nucleomonomer. In various embodiments, the substitute linkages for use in the oligomers of the present invention include phosphodiester, phosphorothioate, methylphosphonate and thionomethylphosphonate linkages. Phosphorothioate and methylphosphonate linkages confer added stability to the oligomer in physiological environments. While not all such linkages in the same oligomer need be identical, particularly preferred oligomers of the invention contain uniformly phosphorothioate linkages or uniformly methylphosphonate linkages.

Oligomers or the segments thereof are conventionally synthesized, and can be prepared using a compound of the invention. The synthetic methods known in the art and described herein can be used to synthesize oligomers containing compounds of the invention, as well as other nucleobases known in the art, using appropriately protected nucleomonomers. Methods for the synthesis of oligomers are found, for example, in Froehler, B., et al., *Nucleic Acids Res.* (1986) 14:5399-5467; *Nucleic Acids Res.* (1988) 16:4831-4839; *Nucleosides and Nucleotides* (1987) 6:287-291; Froehler, B., *Tetrahedron Lett.* (1986) 27:5575-5578; Caruthers, M. H. in Oligodeoxynucleotides-Antisense Inhibitions of Gene Expression (1989), J. S. Cohen, editor, CRC Press, Boca Raton, p 7-24; Reese, C. B. et al., *Tetrahedron Lett.* (1985) 26:2245-2248. Synthesis of the methylphosphonate linked oligomers via methyl phosphonamidite chemistry has also been described (Agrawal, S. et al., *Tetrahedron Lett.* (1987) 28:3539-3542; Klem, R. E., et al., International Publication Number WO 92/07864).

As disclosed herein, the invention provides "conjugates" of oligomers. For instance, the oligomers can be covalently linked to various functional components such as, stabilizing moieties, fluorophores, quenchers, intercalators, and substances which interact specifically with the minor groove of the DNA double helix (minor groove binders, "MGB"). Other chosen conjugate moieties, can be labels such as radioactive, fluorescent, enzyme, or moieties which facilitate cell association using cleavage linkers and the like. Suitable radiolabels include $^{32}P$, $^{35}S$, $^{3}H$ and $^{14}C$; and suitable fluorescent labels include fluorescein, resorufin, rhodamine, BODIPY (Molecular Probes) and texas red; suitable enzymes include alkaline phosphatase and horseradish peroxidase. Additional fluorophores are set forth herein and are generally recognized in the art. Other covalently linked moieties include biotin, antibodies or antibody fragments, and proteins, e.g., transferrin and the HIV Tat protein.

As discussed herein and recognized in the art, the oligomers can be derivatized through any convenient linkage. For example, minor groove binders, fluorophores, quenchers and intercalators, such as acridine or psoralen can be linked to the oligomers of the invention through any available— OH or —SH, e.g., at the terminal 5'-position of the oligomer, the 2'-positions of RNA, or an OH, $NH_2$, COOH or SH incorporated into the 5-position of Pyrimidines. A derivatized form which contains, for example, —$CH_2CH_2NH_2$, —$CH_2CH_2CH_2OH$ or —$CH_2CH_2CH_2SH$ in the 5-position is of use in the present invention. Conjugates including polylysine or lysine can be synthesized as described and can further enhance the binding affinity of an oligomer to its target nucleic acid sequence (Lemaitre, M. et al., *Proc Natl Acad Sci* (1987) 84:648-652; Lemaitre, M. et al., *Nucleosides and Nucleotides* (1987) 6:311-315).

A wide variety of substituents can be attached, including those bound through linkages or substitute linkages. The —OH moieties in the phosphodiester linkages of the oligomers can be replaced by phosphate groups, protected by standard protecting groups, or coupling groups to prepare additional linkages to other nucleomonomers, or can be bound to the conjugated substituent. The 5'-terminal OH can be phosphorylated; the 2'-OH or OH substituents at the 3'-terminus can also be phosphorylated. The hydroxyls can also be derivatized to standard protecting groups.

Oligomers of the invention can be covalently derivatized to moieties that facilitate cell association using cleavable linkers. Linkers used for such conjugates can include disulfide linkages that are reduced after the oligomer-transport agent conjugate has entered a cell. Disulfide-containing linkers of this type have a controllable half life. Such linkers are stable under extracellular conditions relative to intracellular conditions due to the redox potential of the disulfide linkage.

Donor and Acceptor Moieties
Quenchers

Exemplary solid supports and oligomers of the invention include a quencher covalently attached thereto, optionally through a linker. In various embodiments, the quencher is a moiety having a structure according to Formula I or II:

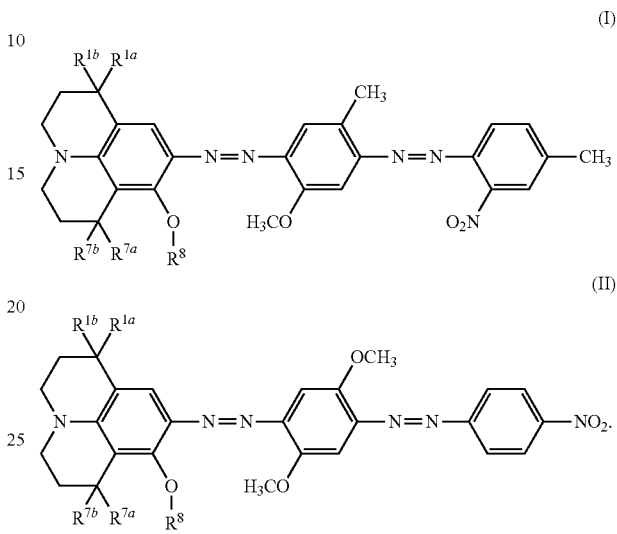

wherein $R^{1a}$, $R^{1b}$, $R^{7a}$, $R^{7b}$ and $R^8$ are as defined herein; and $R^8$ comprises a linkage site covalently bound (directly or through a linker) to a solid support, a linkage site covalently bound (directly or through a linker) to an oligomer, or both.

One of the advantages of the compounds of the invention is that a wide range of energy donor molecules can be used in conjunction with the quencher-functionalized solid supports and oligomers. A vast array of fluorophores is known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.,* 40: 83-114 (1971); Stryer, L. *Ann. Rev. Biochem.,* 47: 819-846 (1978); Wang et al., *Tetrahedron Letters* 31: 6493-6496 (1990); Wang et al., *Anal. Chem.* 67: 1197-1203 (1995).

A non-limiting list of exemplary donors that can be used in conjunction with the quenchers of the invention is provided in Table 1.

TABLE 1

Suitable moieties that can be selected
as donors or acceptors in donor-acceptor energy transfer pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumaran 151)

TABLE 1-continued

Suitable moieties that can be selected
as donors or acceptors in donor-acceptor energy transfer pairs cyanine dyes
cyanosine
4',6-diaminidino-2-phenylindole (DAPI)
5',5"-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
metal chelates, e.g., lanthanide chelates (e.g., europium terbium chelates), ruthenium chelates There is a great deal of practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

Generally, it is preferred that an absorbance band of the quencher substantially overlap the fluorescence emission band of the donor. When the donor (fluorophore) is a component of a probe that utilizes donor-acceptor energy transfer, the donor fluorescent moiety and the quencher (acceptor) of the invention are preferably selected so that the donor and acceptor moieties exhibit donor-acceptor energy transfer when the donor moiety is excited. One factor to be considered in choosing the fluorophore-quencher pair is the efficiency of donor-acceptor energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of energy transfer between the donor-acceptor pair can also be adjusted by changing the ability of the donor and acceptor groups to dimerize or closely associate. If the donor and acceptor moieties are known or determined to closely associate, an increase or decrease in association can be promoted by adjusting the length of a linker moiety, or of the probe itself, between the donor and acceptor. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is generally covalently bound to the probe species. The ligand then binds to another molecules (e.g., streptavidin) molecule, which is either inherently detectable or covalently bound to a signal system, such as a fluorescent compound, or an enzyme that produces a fluorescent compound by conversion of a non-fluorescent compound. Useful enzymes of interest as labels include, for example, hydrolases, particularly phosphatases, esterases and glycosidases, hydrolases, peptidases or oxidases, particularly peroxidases, and. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

Donors of use in conjunction with the quenchers of the invention, include, for example, xanthene dyes, including fluoresceins, cyanine dyes and rhodamine dyes. Many suitable forms of these compounds are widely available commercially with substituents on their phenyl moieties, which can be used as the site for bonding or as the bonding functionality for attachment to a nucleic acid. Another group of fluorescent compounds of use in conjunction with the quenchers of the invention are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other donors include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

For clarity of illustration, the discussion below focuses on attaching quenchers and fluorophores to nucleic acids. The focus on nucleic acid probes is not intended to limit the scope of probe molecules to which quenchers can be attached. Those of skill in the art will appreciate that quenchers can also be attached to small molecules, proteins, peptides, synthetic polymers, solid supports and the like using standard synthetic chemisty.

In an exemplary embodiment, in which the probe is a nucleic acid probe, the fluorophore is a Quasar® dye (Biosearch Technologies, Inc.). The fluorophore is preferably attached to either the 3'- or the 5'-terminus of the nucleic acid, although internal sites are also accessible and have utility for selected purposes. Whichever terminus the fluorophore is attached to, the quencher will generally be attached to its antipode, or at a position internal to the nucleic acid chain. Donor groups are preferably introduced using an amidite derivative of the donor. Alternatively, donor groups comprising reactive functional groups (e.g., isothiocyanates, active esters, etc.) can be introduced via reaction with a reactive functional group on a tether or linker arm attached to the nucleic acid (e.g., hexyl amine).

In yet another preferred embodiment, the donor moiety can be attached at the 3'-terminus of a nucleic acid by the use of a derivatized synthesis support. For example, TAMRA (tetramethylrhodamine carboxylic acid) is attached to a nucleic acid 3'-terminus using a solid support that is derivatized with an analogue of this fluorophore (Biosearch Technologies, Inc.)

In view of the well-developed body of literature concerning the conjugation of small molecules to nucleic acids, many other methods of attaching donor/acceptor pairs to nucleic acids will be apparent to those of skill in the art. For example, rhodamine and fluorescein dyes are conveniently attached to the 5'-hydroxyl of a nucleic acid at the conclusion of solid phase synthesis by way of dyes derivatized with a phosphoramidite moiety (see, for example, Woo et al., U.S. Pat. No. 5,231,191; and Hobbs, Jr., U.S. Pat. No. 4,997,928).

More specifically, there are many linker moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink™ II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Reactive Functional Groups

The components of the compounds of the invention (e.g., linkers, nucleoside, nucleotide, oligonucleotide, nucleic acid, carrier molecule, and solid support) may be linked through linkage sites formed by reaction of a first and a second reactive functional group.

The reactive functional groups are of complementary reactivity, and they react to form a covalent link between two components of the compounds, referred to herein as a linkage site. For example, compounds according to Formula (I) or (II) wherein $R^x$ or $R^s$ is a reactive functional group can be reacted with a reactive functional group of complementary reactivity on another component (such as a linker, nucleoside, nucleotide, oligonucleotide, nucleic acid, carrier molecule, and solid support) to covalently join the components through the resulting linkage site. The reactive functional group of complementary reactivity can be located at any position of the other component (linker, nucleoside etc.), e.g., an alkyl or heteroalkyl an aryl or heteroaryl nucleus or a substituent on an aryl or heteroaryl nucleus. In various embodiments, when the reactive group is attached to an alkyl (or heteroalkyl), or substituted alkyl (or heteroalkyl) chain, the reactive group is preferably located at a terminal position of the chain.

Reactive groups and classes of reactions useful in practicing the present invention are generally those that are well known in the art of bioconjugate chemistry. Currently favored classes of reactions available with reactive precursors of the oligomers of the invention are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

By way of example, reactive functional groups of use in the present invention include, but are not limited to olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

Useful reactive functional group conversions include, for example:

(a) carboxyl groups which are readily converted to various derivatives including, but not limited to, active esters (e.g., N-hydroxysuccinimide esters, N-hydroxybenztriazole esters, thioesters, p-nitrophenyl esters), acid halides, acyl imidazoles, alkyl, alkenyl, alkynyl and aromatic esters;

(b) hydroxyl groups, which can be converted to esters, ethers, halides, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with acyl halides;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble the oligomer of the invention. Alternatively, a reactive functional group can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Covalent Bonding Moiety

Included in some of the oligomers of the invention is a reactive functional group moiety which is capable of effecting at least one covalent bond between the oligomer and a target sequence. Multiple covalent bonds can also be formed by providing a multiplicity of such moieties. The covalent bond is preferably to a nucleobase residue in the target strand, but can also be made with other portions of the target, including the sugar or phosphodiester.

The reaction nature of the moiety which effects crosslinker determines the nature of the target in the duplex. Preferred crosslinker moieties include acylating and alkylating agents, and, in particular, those positioned relative to the sequence specificity-conferring portion so as to permit reaction with the target location in the strand.

The crosslinker moiety can conveniently be placed as an analogous pyrimidine or purine residue in the sequence of the oligomer. The placement can be at the 5'- and/or 3'-ends, the internal portions of the sequence, or combinations of the above. Placement at the termini to permit enhanced flexibility is preferred. Analogous moieties can also be attached to peptide backbones.

Exemplary of alkylating moieties that are useful in the invention include $N^4,N^4$-ethanocytosine and $N^6,N^6$-ethanoadenine.

It is clear that the nucleobase need not be a purine or pyrimidine; indeed the moiety to which the reactive function is attached need not be a nucleobase at all and may be a sugar, a linker, a quencher, a stabilizing moiety a fluorophore or some combination of these components of the oligomers of the invention. Any means of attaching the reactive group is satisfactory so long as the positioning is correct.

Synthesis

Compounds of the invention (such as solid supports, monomers (e.g., phosphoramidites) and oligomers of the invention or the segments thereof) are generally conventionally synthesized. See, for example, U.S. Pat. Nos. 7,019,129; 8,466,266; and 7,879,986. The synthetic methods known in the art and described herein can be used to synthesize oligomers containing compounds of the invention, as well as other nucleobases known in the art, using appropriately protected nucleomonomers. Methods for the synthesis of oligomers are found, for example, in Froehler, B., et al., *Nucleic Acids Res.* (1986) 14:5399-5467; *Nucleic Acids Res.* (1988) 16:4831-4839; *Nucleosides and Nucleotides* (1987) 6:287-291; Froehler, B., Tetrahedron Letters (1986) 27:5575-5578; Caruthers, M. H. in Oligodeoxynucleotides-Antisense Inhibitions of Gene Expression (1989), J. S. Cohen, editor, CRC Press, Boca Raton, p 7-24; Reese, C. B. et al., Tetrahedron Letters (1985) 28:2245-2248. Synthesis of the methylphosphonate linked oligomers via methyl phosphonamidite chemistry has also been described (Agrawal, S. et al., *Tetrahedron Letters* (1987) 28:3539-3542; Klem, R. E., et al., International Publication Number WO 92/07864).

Figure 2:
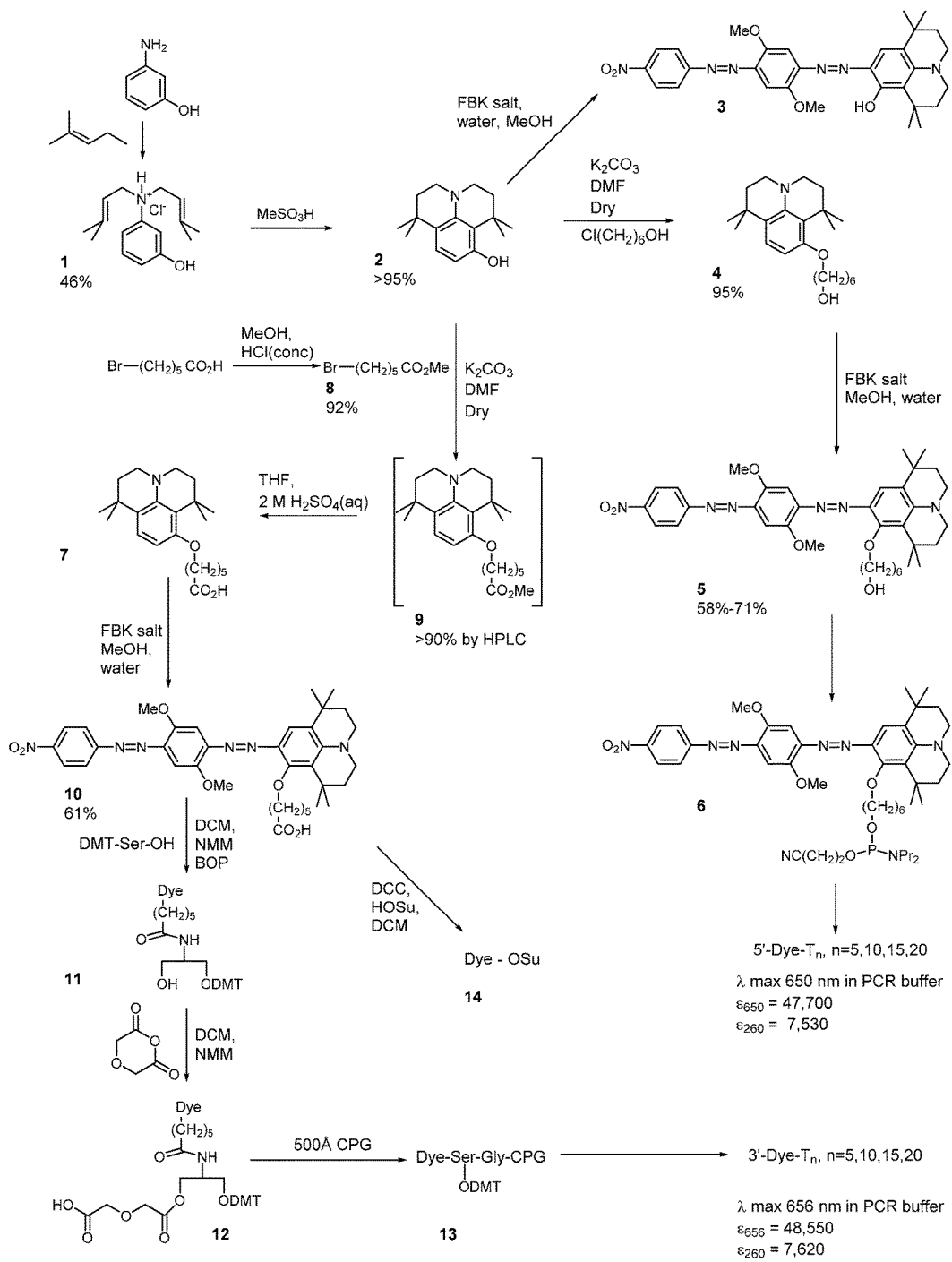
FIG. 2 is a scheme outlining the synthesis of exemplary compounds of the invention.

An exemplary synthesis of various compounds of the invention is set forth in FIG. 2 and Example 1.

In an exemplary embodiment, nucleomonomers are directly incorporated into oligomers or a convenient fragment thereof using standard synthesis conditions and reagents.

Exemplary linkages made by this method include phosphodiester, phosphorothioate, phosphoroamidate, methylphosphonate, phosphorodithioate, carbonate, morpholino carbamate and sulfonate.

In various embodiments, synthesis involves synthesis of short synthons (dimers, trimers, etc.) starting with an appropriate precursor. This approach is suitable for synthesis of linkages including N-methylhydroxylamine, dimethylhydrazo, sulfamate, carbamate, sulfonate, sulfonamide, formacetal thioformacetal and carbonate.

Oligomers of the invention can be synthesized by any suitable chemistry including amidite, triester or hydrogen phosphonate coupling methods and conditions. The oligomers are preferably synthesized from appropriate starting synthons which are preferably protected at the 5'-position with DMT, MMT, FMOC (9-fluorenylmethoxycarbonyl), PACO (phenoxyacetyl), a say' ether such as TBDMS (t-butyldiphenylsilyl) or TMS (trimethylsilyl) and activated at the 3'-position is an ester, H-phosphonate, an amidite such as β-cyanoethylphosphoramidite, a silyl ether such as TBDMS or TMS or t-butyldiphenyl. Alternatively, appropriate uridine or cytidine precursors such as blocked 5-iodo-2'-deoxyuridine, 5-iodo-2'-O-alkyluridine, 5-bromo-2'-deoxyuridine, 5-trifluoromethanesulfonate-2'-deoxyuridine, 5-bromo-2'-O-alkyluridine or blocked and protected 5-iodo-2'-deoxycytidine, 5-bromo-2'-deoxycytidine, 5-trifluoromethanesulfonate-2'-deoxycytidine, 5-iodo-2'-O-alkylcytidine, 5-bromo-2'-O-alkylcytidine can be conveniently incorporated into short oligomers such as dimer, trimer, tetramer, pentamer or longer synthons that are subsequently derivatized to yield suitable synthons and longer oligomers.

Exemplary synthesis of oligomers containing about 4 or more nucleomonomer residues are accomplished using synthons such as monomers, dimers or trimers that carry a coupling group suitable for use with amidite, H-phosphonate or triester chemistries. The synthon can be used to link the components of the oligomer via a phosphodiester or phosphorous-containing linkage other than phosphodiester (e.g., phosphorothioate, methylphosphonate, thionomethylphosphonate, phosphoramidate and the like).

Synthesis of other nonphosphorous-containing substituted linkages can be accomplished using appropriate precursors as known in the art.

Once the desired nucleic acid is synthesized, it is preferably cleaved from the solid support on which it was synthesized and treated, by methods known in the art, to remove any protecting groups present (e.g., 60° C., 5 h, concentrated ammonia). In those embodiments in which a base-sensitive group is attached to the nucleic acids (e.g., TAMRA), the deprotection will preferably use milder conditions (e.g., butylamine:water 1:3, 8 hours, 70° C.). Deprotection under these conditions is facilitated by the use of quick deprotect amidites (e.g., dC-acetyl, dG-dmf).

Following cleavage from the support and deprotection, the nucleic acid is purified by any method known in the art, including chromatography, extraction and gel purification. In a preferred embodiment, the nucleic acid is purified using HPLC. The concentration and purity of the isolated nucleic acid is preferably determined by measuring the optical density at 260 nm in a spectrophotometer.

Assays and Oligomeric Probes of the Invention

In various embodiments, the present invention provides an oligomer of use in one or more assay formats. In selected embodiments the oligomer participates in the generation of a detectable signal upon association with or dissociation from its target. The oligomeric probes of the invention are not limited in use to any particular assay format. Accordingly, the following description is intended to illustrate exemplary assays formats in which the oligomers of the invention find use, and is not intended to be limiting of the assay formats in which the oligomers are of use.

Assays

The following discussion is generally relevant to the assays described herein. This discussion is intended to illustrate the invention by reference to certain preferred embodiments and should not be interpreted as limiting the scope of probes and assay types in which the compounds of the invention find use. Other assay formats utilizing the compounds of the invention will be apparent to those of skill in the art.

In general, to determine the concentration of a target molecule, such as, for example, a nucleic acid of unknown quantity, it is preferable to first obtain reference data in which constant amounts of probe are contacted with nucleic acid standards spanning a range of known quantities. The intensity of fluorescence emission from each of the reference mixtures is used to derive a graph or standard curve, in which the unknown concentration is compared to the intensity of the known standards. For example, a probe that: a) hybridizes to a sequence within the target nucleic acid; b) has fluorophore and quencher modifications upon the 5' and 3' termini being the sites of labeling; and c) has fluorogenic character that is quenched in an unbound conformation and then releases signal upon binding to the target nucleic acid, can be used to obtain such reference data. Such a probe gives a characteristic fluorescence emission in which the signal increases as the concentration of target nucleic acid increases. Then, a sample with an unknown quantity of target is contacted with the probe, and the fluorescence intensity from the mixture is determined. The intensity of fluorescence emission is then compared with the reference standards to obtain the concentration of the target in the test mixture.

Multiplex Analyses

In another embodiment, the solid supports and oligomers of the invention are utilized as a probe or a component of one or more probes used in a multiplex assay for detecting one or more species in a mixture.

Probes based on the solid supports or oligomers of the invention are particularly useful in performing multiplex-type analyses and assays. In a typical multiplex analysis, two or more distinct species (or regions of one or more species) are detected using two or more probes, wherein each of the probes is labeled with a different fluorophore. Preferred species used in multiplex analyses relying on donor-acceptor energy transfer meet at least two criteria: the fluorescent species is bright and spectrally well-resolved; and the energy transfer between the fluorescent species and the quencher is efficient.

The solid supports and oligomers of the invention allow for the design of multiplexed assays in which more than one fluorescent reporter is partnered with one or more quencher structures. A number of different multiplexed assays using the solid supports or oligomers of the invention will be apparent to one of skill in the art. In one exemplary assay, each of at least two distinct fluorescent reporters are paired with the same type of quencher structure on their respective oligomers, to modulate the signal through either FRET or contact quenching. Alternatively, an assay can be practiced in which at least two distinct fluorescent reporters are partnered with distinct quencher structures, to which the fluorescent properties are better "matched." The fluorophores can be bound to the same molecule as the quencher or to a different molecule. Moreover, similar to the quencher and the fluorophores, the carrier molecules of use in a particular assay system, such as the oligo sequence that covelently tethers the fluorophore and quencher, can either be the same or different.

In addition to the mixtures described above, the present invention also provides a qualitative method for detecting the presence a particular molecular species. The method includes: (a) contacting the species with a mixture containing a solid support or oligomer of the invention; and (b) detecting a change in a fluorescent property of one or more component of the resulting mixture, thereby detecting the presence the molecular species.

The simultaneous use of two or more probes using donor-acceptor energy transfer is known in the art. For example, multiplex assays using nucleic acid probes with different sequence specificities have been described. Fluorescent probes have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. *Science* 279:1228-1229 (1998)). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi et al. *Nature Biotechnology* 16: 49-53 (1998)) have described the simultaneous use of four differently labeled molecular beacons for allele discrimination, and Lee et al., *BioTechniques* 27: 342-349 (1999) have described seven color homogenous detection of six PCR products.

The quenchers of the present invention can be used in multiplex assays designed to detect and/or quantify substantially any species, including, for example, whole cells, viruses, proteins (e.g., enzymes, antibodies, receptors), glycoproteins, lipoproteins, subcellular particles, organisms (e.g., *Salmonella*), nucleic acids (e.g., DNA, RNA, and analogues thereof), polysaccharides, lipopolysaccharides, lipids, fatty acids, non-biological polymers and small molecules (e.g., toxins, drugs, pesticides, metabolites, hormones, alkaloids, steroids).

Nucleic Acid Probes

The solid supports and oligomers of the invention are useful nucleic-acid probes and they can be used as components of detection agents in a variety of DNA amplification/quantification strategies including, for example, 5'-nuclease assay, Strand Displacement Amplification (SDA), Nucleic Acid Sequence-Based Amplification (NASBA), Rolling Circle Amplification (RCA), as well as for direct detection of targets in solution phase or solid phase (e.g., array) assays. Furthermore, the solid supports and oligomers can be used in probes of substantially any format, including, for example, format selected from molecular beacons, Scorpion Probes™, Sunrise Probes™, conformationally assisted probes, light up probes, Invader Detection probes, and TaqMan™ probes. See, for example, Cardullo, R., et al., *Proc. Natl. Acad. Sci. USA*, 85:8790-8794 (1988); Dexter, D. L., *J. Chem. Physics*, 21:836-850 (1953); Hochstrasser, R. A., et al., *Biophysical Chemistry*, 45:133-141 (1992); Selvin, P., *Methods in Enzymology*, 246:300-334 (1995); Steinberg, I., *Ann. Rev. Biochem.*, 40:83-114 (1971); Stryer, L., *Ann. Rev. Biochem.*, 47:819-846 (1978); Wang, G., et al., *Tetrahedron Letters*, 31:6493-6496 (1990); Wang, Y., et al., *Anal. Chem.*, 67:1197-1203 (1995); Debouck, C., et al., in supplement to *nature genetics*, 21:48-50 (1999); Rehman, F. N., et al., *Nucleic Acids Research*, 27:649-655 (1999); Cooper, J. P., et al., *Biochemistry*, 29:9261-9268 (1990); Gibson, E. M., et al., *Genome Methods*, 6:995-1001 (1996); Hochstrasser, R. A., et al., *Biophysical Chemistry*, 45:133-141 (1992); Holland, P. M., et al., *Proc Natl. Acad. Sci USA*, 88:7276-7289 (1991); Lee, L. G., et al., *Nucleic Acids Rsch.*, 21:3761-3766 (1993); Livak, K. J., et al., *PCR Methods and Applications*, Cold Spring Harbor Press (1995); Vamosi, G., et al., *Biophysical Journal*, 71:972-994 (1996); Wittwer, C. T., et al., *Biotechniques*, 22:176-181 (1997); Wittwer, C. T., et al., *Biotechniques*, 22:130-38 (1997); Giesendorf, B. A. J., et al., *Clinical Chemistry*, 44:482-486 (1998); Kostrikis, L. G., et al., *Science*, 279:1228-1229 (1998); Matsuo, T., *Biochemica et Biophysica Acta*, 1379:178-184 (1998); Piatek, A. S., et al., *Nature Biotechnology*, 16:359-363 (1998); Schofield, P., et al., *Appl. Environ. Microbiology*, 63:1143-1147 (1997); Tyagi S., et al., *Nature Biotechnology*, 16:49-53 (1998); Tyagi, S., et al., *Nature Biotechnology*, 14:303-308 (1996); Nazarenko, I. A., et al., *Nucleic Acids Research*, 25:2516-2521 (1997); Uehara, H., et al., *Biotechniques*, 26:552-558 (1999); D. Whitcombe, et al., *Nature Biotechnology*, 17:804-807 (1999); Lyamichev, V., et al., *Nature Biotechnology*, 17:292 (1999); Daubendiek, et al., *Nature Biotechnology*, 15:273-277 (1997); Lizardi, P. M., et al., *Nature Genetics*, 19:225-232 (1998); Walker, G., et al., *Nucleic Acids Res.*, 20:1691-1696 (1992); Walker, G. T., et al., *Clinical Chemistry*, 42:9-13 (1996); and Compton, J., *Nature*, 350:91-92 (1991).

Thus, the present invention provides a method for detecting a nucleic acid target sequence. The method includes: (a) contacting the target sequence with a detector nucleic acid (e.g., an oligomer of the invention); (b) hybridizing the target binding sequence to the target sequence, thereby altering the conformation of the detector nucleic acid, causing a change in a fluorescence parameter; and (c) detecting the change in the fluorescence parameter, thereby detecting the nucleic acid target sequence.

In the methods described herein, unless otherwise noted, a preferred detector nucleic acid includes a single-stranded target binding sequence. The binding sequence has linked thereto: i) a fluorophore; and ii) a quencher. The binding sequence has optionally further linked thereto a stabilizing moiety. Moreover, prior to its hybridization to a complementary sequence, the detector nucleic acid is preferably in a conformation that allows donor-acceptor energy transfer between the fluorophore and the quencher when the fluorophore is excited. Furthermore, in each of the methods described in this section, a change in fluorescence is detected as an indication of the presence of the target sequence. The change in fluorescence is preferably detected in-real time.

Presently preferred nucleic acid probes do not require the nucleic acid to adopt a secondary structure for the probe to function. In this method, and unless otherwise noted, the other methods described in this section, the detector nucleic acid can assume substantially any intramolecularly associated secondary structure, but this structure is preferably a member selected from hairpins, stem-loop structures, pseudoknots, triple helices and conformationally assisted structures. Moreover, the intramolecularly base-paired secondary structure preferably comprises a portion of the target binding sequence.

In another aspect, the invention provides a method for detecting amplification of a target sequence. The method involves the use of an amplification reaction such as PCR. An exemplary amplification reaction includes one or more of the following steps:

(a) hybridizing a sample nucleic acid comprising the target sequence of interest with PCR primers that flank the target sequence;

(b) extending the hybridized primers with a polymerase to produce the PCR product, and separating the two strands of the PCR product to make accessible the sense and antisense strands of the target sequence;

(c) hybridizing a detector nucleic acid to the sense or antisense strand of the target sequence in the PCR product, wherein the detector nucleic acid includes:
  i) a single stranded target binding sequence that is complementary to at least a portion of the sense or antisense strand of the target sequence in the PCR product, and hybridizes to a region between the PCR primers;
  ii) a fluorophore; and
  iii) a quencher of the invention;
  wherein prior to its hybridization to the target sequence, the detector nucleic acid is in a conformation allowing donor-acceptor energy transfer between the fluorophore and the quencher when the fluorophore is excited;

thereby altering the conformation of the detector nucleic acid (for example, linearizing any secondary structure or random coil conformations that contribute to the quenching efficiency), causing a change in a fluorescence parameter (such as the signal intensity); and (d) measuring the change in the fluorescence parameter to detect the target sequence and its amplification.

Optionally, the change in the fluorescence parameter can be made permanent if the polymerase encounters the hybridized detector nucleic acid during primer extension (step (b) above) and hydrolyzes the oligomer tethering the fluorophore and quencher, such as through a secondary nuclease activity of the polymerase.

In yet a further aspect, the invention provides a method of ascertaining whether a first nucleic acid and a second nucleic acid hybridize. In this method, the first nucleic acid is an oligomer (in solution or attached to a solid support) according to the invention. The method includes: (a) contacting the first nucleic acid with the second nucleic acid; (b) detecting an alteration in a fluorescent property of a member selected from the first nucleic acid, the second nucleic acid and a combination thereof, thereby ascertaining whether the hybridization occurs.

In various embodiments, the present invention provides probes and methods of use in detecting polymorphism in nucleic acid target sequences. Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

In an exemplary embodiment, a probe of the invention is utilized to detect a single nucleotide polymorphism. A single nucleotide polymorphism occurs at a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

An oligomer of the invention bearing both a quencher and a fluorophore can be used or, alternatively, one or more of the nucleic acids can be singly labeled with a single member of an energy transfer pair (e.g. a quencher or fluorophore).

When a nucleic acid singly labeled with a quencher is the probe, the interaction between the first and second nucleic acids can be detected by observing the interaction between the quencher and the nucleic acid or, more preferably, the quenching by the quencher of the fluorescence of a fluorophore attached to the second nucleic acid.

In some embodiments, a ground state complex between a quencher of the invention and a fluorophore is formed. In an exemplary embodiment, both the quencher and fluorophore are conjugated to the same nucleic acid oligomer.

In addition to their general utility in probes designed to investigate nucleic acid amplification, polymorphism and detection and quantification, the present solid supports and oligomers can be used in substantially any nucleic acid probe format now known or later discovered. For example, the solid supports and oligomers of the invention can be incorporated into probe motifs, such as Taqman™ probes (Held et al., *Genome Res.* 6: 986-994 (1996), Holland et al., *Proc. Nat. Acad. Sci. USA* 88: 7276-7280 (1991), Lee et al., *Nucleic Acids Res.* 21: 3761-3766 (1993)), molecular beacons (Tyagi et al., *Nature* Biotechnology 14:303-308 (1996), Jayasena et al., U.S. Pat. No. 5,989,823, issued Nov. 23, 1999)) scorpion probes (Whitcomb et al., *Nature Biotechnology* 17: 804-807 (1999)), sunrise probes (Nazarenko et al., *Nucleic Acids Res.* 25: 2516-2521 (1997)), conformationally assisted probes (Cook, R., copending and commonly assigned U.S. patent Application 2007/0059752, filed Jun. 9, 1999), peptide nucleic acid (PNA)-based light up probes (Kubista et al., WO 97/45539, December 1997), double-strand specific DNA dyes (Higuchi et al., *Bio/Technology* 10: 413-417 (1992), Wittwer et al., *BioTechniques* 22: 130-138 (1997)) and the like. These and other probe motifs with which the present quenchers can be used are reviewed in Nonisotopic DNA Probe Techniques, Academic Press, Inc. 1992.

The oligomers for use in the probes of the invention can be any suitable size, and are preferably in the range of from about 2 to about 100 nucleotides, more preferably from about 10 to about 80 nucleotides and more preferably still, from about 10 to about 40 nucleotides. In the dual labeled (fluorophore-quencher) probes, the donor moiety is preferably separated from the quencher by at least about 6, preferably at least about 8, preferably at least about 10 nucleotides, and more preferably by at least about 15 nucleotides. In various embodiments donor moiety is preferably attached to either the 3'- or 5'-terminal nucleotides of the probe. The quencher moiety is also preferably attached to either the 3'- or 5'-terminal nucleotides of the probe. More preferably, the donor and acceptor moieties are attached to the 3'- and 5'- or 5'- and 3'-terminal nucleotides of the probe, respectively, although internal placement is also useful.

The precise sequence and length of a nucleic acid probe of the invention depends in part on the nature of the target polynucleotide to which it binds. The binding location and length may be varied to achieve appropriate annealing and melting properties for a particular embodiment. Guidance for making such design choices can be found in many art-recognized references.

In some embodiments, the 3'-terminal nucleotide of the nucleic acid probe is blocked or rendered incapable of extension by a nucleic acid polymerase. Such blocking is conveniently carried out by the attachment of a donor or acceptor moiety to the terminal 3'-position of the nucleic acid probe, either directly or by a linker moiety.

The nucleic acid can comprise DNA, RNA or chimeric mixtures or derivatives or modified versions thereof. Both the probe and target nucleic acid can be present as a single strand, duplex, triplex, etc. Moreover, the nucleic acid can be modified at the nucleobase moiety, sugar moiety, or phosphate backbone with other groups such as radioactive labels, minor groove binders, intercalating agents, acetylinically unsaturated hydrocarbons, fluoralkyl groups, donor and/or acceptor moieties and the like.

The oligomers of the invention are useful as primers that are discrete sequences or as primers with a random sequence. Random sequence primers are generally about 6 or 7 nucleomonomers in length. Such primers can be used in various nucleic acid amplification protocols (PCR, ligase chain reaction, etc) or in cloning protocols. Substitutions on the 5' end of the invention generally do not interfere with the capacity of the oligomer to function as a primer. Oligomers of the invention having 2'-modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized with chelating agents such as EDTA, DTPA or analogs of 1,2-diaminocyclohexane acetic acid can be utilized in various in vitro diagnostic assays as described (U.S. Pat. Nos. 4,772,548, 4,707,440 and 4,707,352). Alternatively, oligomers of the invention can be derivatized with crosslinker agents such as 5-(3-iodoacetamidoprop-1-yl)-2'-deoxyuridine or 5-(3-(4-bromobutyramido)prop-1-yl)-2'-deoxyuridine and used in various assay methods or kits as described (International Publication No. WO 90/14353).

In addition to the foregoing uses, the ability of the oligomers to inhibit gene expression can be verified in in vitro systems by measuring the levels of expression in subject cells or in recombinant systems, by any suitable method (Graessmann, M., et al., *Nucleic Acids Res.* (1991) 19:53-59).

Conditions that favor hybridization between oligomer of the present invention and target nucleic acid molecules can be determined empirically by those skilled in the art, and can include optimal incubation temperatures, salt concentrations, length and nucleobase compositions of oligonucleotide analogue probes, and concentrations of oligomer and nucleic acid molecules of the sample. Preferably, hybridization is performed in the presence of at least one millimolar magnesium and at a pH that is above 6.0. In some embodiments, it may be necessary or desirable to treat a sample to render nucleic acid molecules in the sample single-stranded prior to hybridization. Examples of such treatments include, but are not limited to, treatment with base (preferably followed by neutralization), incubation at high temperature, or treatment with nucleases.

In addition, because the salt dependence of hybridization to nucleic acids is largely determined by the charge density of the backbone of a hybridizing oligonucleotide analogue, incorporating nonstandard nucleotide analogs into the oligomer of the present invention can increase or decrease the salt dependence of hybridization. This modulation can be used to advantage in the methods of the present invention where it can in some aspects be desirable to be able to increase the stringency of hybridization by changing salt conditions, for example, or release a hybridized nucleic acid by reducing the salt concentration. In yet other aspects of the present invention, it can be desirable to have high-affinity binding of an oligonucleotide analogue of the present invention to a nucleic acid in very low salt. In this case, positioning nucleotide monomers with uncharged backbone moieties into an oligonucleotide of the present invention is advantageous.

The high degree of specificity of oligomers of the present invention in binding to target nucleic acid molecules allow the practitioner to select hybridization conditions that can favor discrimination between nucleic acid sequences that comprise a stretch of sequence that is completely complementary to at least a portion of one or more oligomer and target nucleic acid molecules that comprise a stretch of sequence that comprises a small number of non-complementary nucleobases within a substantially complementary sequence. For example, hybridization or wash temperatures can be selected that permit stable hybrids between oligomer of the present invention and target nucleic acid molecules that are completely complementary along a stretch of sequence but promote dissociation of hybrids between oligomer of the present invention and target nucleic acid molecules that are not completely complementary, including those that comprise one or two nucleobase mismatches along a stretch of complementary sequence. The selection of a temperature for hybridization and washes can be dependent, at least in part, on other conditions, such as the salt concentration, the concentration of oligomer and target nucleic acid molecules, the relative proportions of oligomer to target nucleic acid molecules, the length of the oligomers to be hybridized, the nucleobase composition of the oligomer and target nucleic acid molecules, the monomer composition of the oligonucleotide analogue molecules, etc. In addition, when selecting for conditions that favor stable hybrids of completely complementary molecules and disfavor stable hybrids between oligomer and target nucleic acid molecules that are mismatched by one or more nucleobases, additional conditions can be taken into account, and, where desirable, altered, including but not limited to, the length of the oligonucleotide analogue to be hybridized, the length of the stretch of sequence of complementarity between oligomer and target nucleic acid molecules, the number of non-complementary nucleobases within a stretch of sequence of complementarity, the identity of mismatched nucleobases, the identity of nucleobases in the vicinity of the mismatched nucleobases, and the relative position of any mismatched nucleobases along a stretch of complementarity. Those skilled in the art of nucleic acid hybridization would be able to determine favorable hybridization and wash conditions in using oligomer of the present invention for hybridization to target nucleic acid molecules, depending on the particular application. "Favorable conditions" can be those favoring stable hybrids between oligomer and target nucleic acid molecules that are, at least in part, substantially complementary, including those that comprise one or more mismatches.

"Favorable conditions" can be those favoring stable hybrids between oligomer and target nucleic acid molecules that are, at least in part, completely complementary and disfavor or destabilized hybrids between molecules that are not completely complementary.

Using methods such as those disclosed herein, the melting temperature of oligomer of the present invention hybridized to target nucleic acid molecules of different sequences can be determined and can be used in determining favorable conditions for a given application. It is also possible to empirically determine favorable hybridization conditions by, for example, hybridizing target nucleic acid molecules to oligomer that are attached to a solid support and detecting hybridized complexes.

Target nucleic acid molecules that are bound to solid supports or oligomeric probes of the present invention can be conveniently and efficiently separated from unbound nucleic acid molecules of the survey population by the direct or indirect attachment of oligomer probes to a solid support. A solid support can be washed at high stringency to remove nucleic acid molecules that are not bound to oligomer probes. However, the attachment of oligomer probes to a solid support is not a requirement of the present invention. For example, in some applications bound and unbound nucleic acid molecules can be separated by centrifugation through a matrix or by phase separation or some by other forms of separation (for example, differential precipitation) that can optionally be aided by chemical groups incorporated into the oligomer probes (see, for example, U.S. Pat. No. 6,060,242 issued May 9, 2000, to Nie et al.).

Nucleic Acid Capture Probes

In one embodiment, an immobilized nucleic acid comprising a quencher is used as a capture probe. The immobilized nucleic acid optionally further comprises a stabilizing moiety. The nucleic acid probe can be attached directly to a solid support, for example by attachment of the 3'- or 5'-terminal nucleotide of the probe to the solid support. More preferably, however, the probe is attached to the solid support by a linker (supra). The linker serves to distance the probe from the solid support. The linker is most preferably from about 5 to about 30 atoms in length, more preferably from about 10 to about 50 atoms in length.

In various embodiments, the solid support is also used as the synthesis support in preparing the oligomer (probe). The length and chemical stability of the linker between the solid support and the first 3'-unit of nucleic acid play an important role in efficient synthesis and hybridization of support bound nucleic acids. The linker arm is preferably sufficiently long so that a high yield (>97%) can be achieved during automated synthesis. The required length of the linker will depend on the particular solid support used. For example, a six atom linker is generally sufficient to achieve a >97% yield during automated synthesis of nucleic acids when high cross-linked polystyrene is used as the solid support. The linker arm is preferably at least 20 atoms long in order to attain a high yield (>97%) during automated synthesis when CPG is used as the solid support.

Hybridization of a probe immobilized on a solid support generally requires that the probe be separated from the solid support by at least 30 atoms, more preferably at least 50 atoms. In order to achieve this separation, the linker generally includes a spacer positioned between the linker and the 3'-terminus. For nucleic acid synthesis, the linker arm is usually attached to the 3'-OH of the 3'-terminus by an ester linkage which can be cleaved with basic reagents to free the nucleic acid from the solid support.

A wide variety of linkers are known in the art, which may be used to attach the nucleic acid probe to the solid support. The linker may be formed of any compound, which does not significantly interfere with the hybridization of the target sequence to the probe attached to the solid support. The linker may be formed of, for example, a homopolymeric nucleic acid, which can be readily added on to the linker by automated synthesis. Alternatively, polymers such as functionalized polyethylene glycol can be used as the linker. Such polymers are presently preferred over homopolymeric nucleic acids because they do not significantly interfere with the hybridization of probe to the target nucleic acid. Polyethylene glycol is particularly preferred because it is commercially available, soluble in both organic and aqueous media, easy to functionalize, and completely stable under nucleic acid synthesis and post-synthesis conditions.

The linkage sites between the solid support, the linker and the probe are preferably not cleaved during synthesis or removal of nucleobase protecting groups under basic conditions at high temperature. These linkages can, however, be selected from groups that are cleavable under a variety of conditions. Examples of presently preferred linkages include carbamate, ester and amide linkages.

Detection of Nucleic Acids in Samples

Solid supports and oligomers of the present invention can be used for detection of nucleic acids. Such detection methods include: providing a sample, contacting at least one oligonucleotide analogue of the present invention with the sample under conditions that allow hybridization of oligomer to nucleic acid molecules, and detecting one or more nucleic acid molecules of the sample that have hybridized to one or more oligomer of the present invention.

A sample can be from any source, and can be a biological sample, such as a sample from an organism or a group of organisms from the same or different species. A biological sample can be a sample of bodily fluid, for example, a blood sample, serum sample, lymph sample, a bone marrow sample, ascites fluid, pleural fluid, pelvic wash fluid, ocular fluid, urine, semen, sputum, or saliva. A biological sample can also be an extract from cutaneous, nasal, throat, or genital swabs, or extracts of fecal material. Biological samples can also be samples of organs or tissues, including tumors. Biological samples can also be samples of cell cultures, including both cell lines and primary cultures of both prokaryotic and eukaryotic cells.

A sample can be from the environment, such as from a body of water or from the soil, or from a food, beverage, or water source, an industrial source, workplace area, public area, or living area. A sample can be an extract, for example a liquid extract of a soil or food sample. A sample can be a solution made from washing or soaking, or suspending a swab from, articles such as tools, articles of clothing, artifacts, or other materials.

A sample can be an unprocessed or a processed sample; processing can involve steps that increase the purity, concentration, or accessibility of components of the sample to facilitate the analysis of the sample. As nonlimiting examples, processing can include steps that reduce the volume of a sample, remove or separate components of a sample, solubilize a sample or one or more sample components, or disrupt, modify, expose, release, or isolate components of a sample. Nonlimiting examples of such procedures are centrifugation, precipitation, filtration, homogenization, cell lysis, binding of antibodies, cell separation, etc. For example, in some preferred embodiments of the present invention, the sample is a blood sample that is at least partially processed, for example, by the removal of red blood cells, by concentration, by selection of one or more cell or virus types (for example, white blood cells or pathogenic cells), or by lysis of cells, etc.

Exemplary samples include a solution of at least partially purified nucleic acid molecules. The nucleic acid molecules can be from a single source or multiple sources, and can comprise DNA, RNA, or both. For example, a solution of nucleic acid molecules can be a sample that was subjected to any of the steps of cell lysis, concentration, extraction, precipitation, nucleic acid selection (such as, for example, poly A RNA selection or selection of DNA sequences comprising Alu elements), or treatment with one or more enzymes. The sample can also be a solution that comprises synthetic nucleic acid molecules.

An oligomer or solid support of the present invention can be any oligomer format disclosed herein, or any oligomer comprising a monomer, dimer or non nucleic acid component (e.g., linker, fluorophore, quencher, stabilizing moiety) disclosed herein. An oligonucleotide analogue used in the methods of the present invention can be of any length and of any nucleobase composition, and can comprise one or more nucleic acid moieties, peptides, proteins lipids, carbohydrates, steroids, and other biochemical and chemical moieties. An oligonucleotide analogue of the present invention can be provided in solution or bound to a solid support. In some preferred embodiments of the present invention, the oligomer comprise non-standard nucleotide analogues.

Detection methods for bound nucleic acids are well known in the art, and can include the use of a detectable label that is attached to or incorporated into nucleic acid molecules of the survey population or that becomes bound to or incorporated into a hybridized target nucleic acid molecule or hybridized target nucleic acid molecule complex.

Detectable labels for nucleic acid molecules are well-known in the art, and comprise fluorescent molecules such as fluorophores (including those set forth herein), radioisotopes, mass-altered chemical groups, specific binding members such as biotin that can be detected by signal-generating molecules, and the like. Detectable labels can also be incorporated into or attached to oligomer of the present invention, for example, in cases where sandwich hybridization using a signal oligomer is used for detection, or detection is performed using a specific binding member such as an antibody that recognizes oligomer/target nucleic acid molecule complexes. Solid supports can be scanned, exposed to film, visually inspected, etc. to determine the presence of a detectable label and thereby determine the binding of a target nucleic acid molecule to an oligomer immobolized on a solid support such as those of the invention.

Kits

One aspect of the instant invention is the formulation of kits that facilitate the practice of syntheses using the compounds of the invention (such as solid supports of the invention or monomers of the invention) and assays using oligomers of the invention, as described above. The kits of the invention typically comprise a compound of the invention (such as a solid support of the invention or an oligomer of the invention), either present as a chemically reactive species useful for preparing conjugates, or present as a completed oligomer where the oligomer is a specific binding pair member. The kit optionally further comprises one or more buffering agents, typically present as an aqueous solution. The kits of the invention optionally further comprise additional detection reagents, a purification medium for purifying the resulting labeled substance, luminescence standards, enzymes, enzyme inhibitors, organic solvent, or instructions for carrying out an assay of the invention. Other formats for kits will be apparent to those of skill in the art and are within the scope of the present invention.

By way of summary, in exemplary embodiments, the present invention provides:

A compound having a structure according to Formula I or II:

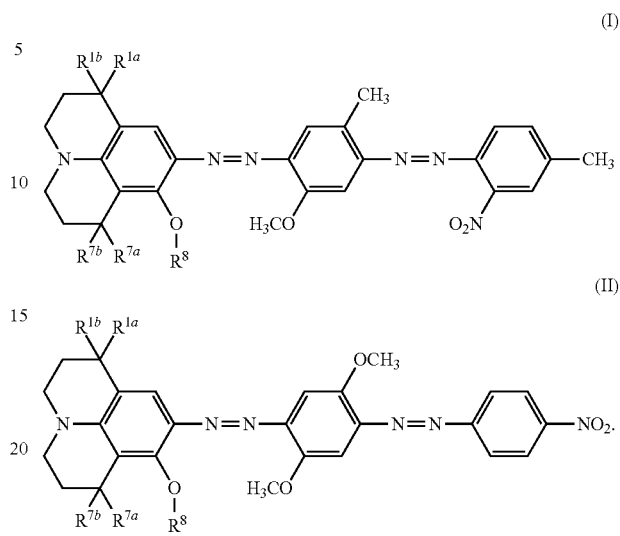

$R^{1a}$, $R^{1b}$, $R^{7a}$, and $R^{7b}$ are independently selected from H, substituted or unsubstituted alkyl, substituted or unsubstituted cycloalkyl, substituted or unsubstituted heteroalkyl, and substituted or unsubstituted heterocycloalkyl. $R^{1a}$ and $R^{1b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl. $R^{7a}$, and $R^{7b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl. At least one of $R^{1a}$, $R^{1b}$, $R^{7a}$, and $R^{7b}$ is not H. $R^8$ is selected from H,

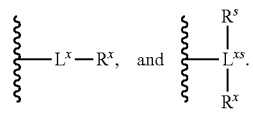

$L^x$ is selected from a bond, substituted or unsubstituted alkyl, substituted or unsubstituted cycloalkyl, substituted or unsubstituted heteroalkyl, and substituted or unsubstituted heterocycloalkyl. $L^{xs}$ is selected from substituted or unsubstituted alkyl, substituted or unsubstituted cycloalkyl, substituted or unsubstituted heteroalkyl, and substituted or unsubstituted heterocycloalkyl. $R^s$ is selected from a protected or unprotected reactive functional group, a linkage site, and a solid support. $R^x$ is selected from a protected or unprotected reactive functional group and a linkage site. Each linkage site is covalently bound to a member independently selected from a nucleoside, a linker to a nucleoside, a nucleotide, a linker to a nucleotide, an oligonucleotide, a linker to an oligonucleotide, a nucleic acid, a linker to a nucleic acid, a carrier molecule, a linker to a carrier molecule, a solid support, and a linker to a solid support.

A compound according to the preceding paragraph, wherein $R^{1a}$ and $R^{1b}$ are independently selected from unsubstituted $C_1$, $C_2$, $C_3$, $C_4$, $C_5$, and $C_6$ alkyl.

A compound according to the preceding paragraph, wherein $R^{1a}$ and $R^{1b}$ are each methyl.

A compound according to any preceding paragraph, wherein $R^{7a}$ and $R^{7b}$ are each H.

A compound according to any preceding paragraph, wherein $R^{7a}$ and $R^{7b}$ are independently selected from unsubstituted $C_1$, $C_2$, $C_3$, $C_4$, $C_5$, and $C_6$ alkyl.

A compound according to any preceding paragraph, wherein $R^{7a}$ and $R^{7b}$ are each methyl.

A compound according to any preceding paragraph, wherein $R^{1a}$ and $R^{1b}$ are each H.

A compound according to any preceding paragraph, wherein $R^{1a}$, $R^{1b}$, $R^{7a}$, and $R^{7b}$ are independently selected from unsubstituted $C_1$, $C_2$, $C_3$, $C_4$, $C_5$, and $C_6$ alkyl.

A compound according to any preceding paragraph, wherein $R^{1a}$, $R^{1b}$, $R^{7a}$, and $R^{7b}$ are each methyl.

A compound according to any preceding paragraph, wherein $L^x$ is selected from unsubstituted $C_1$, $C_2$, $C_3$, $C_4$, $C_5$, $C_6$, $C_7$, $C_8$, $C_9$, and $C_{10}$ alkyl.

A compound according to any preceding paragraph, wherein $L^{xs}$ is substituted heteroalkyl.

A compound according to any preceding paragraph, wherein $R^x$ is selected from a phosphoramidite, —OH, —ODMT, —COOH, an active ester, and —NH$_2$.

A compound according to any preceding paragraph, wherein $R^s$ is selected from —OH, —ODMT, and a linkage site covalently bound to a linker to a solid support.

A compound according to any preceding paragraph, wherein $R^x$ is selected from a phosphoramidite, —OH, —ODMT, —COOH, an active ester, and —NH$_2$.

A compound according to any preceding paragraph, wherein $R^x$ is a linkage site covalently bound to a linker to a nucleoside, wherein the nucleoside has the structure:

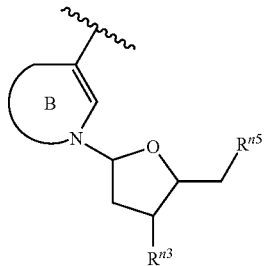

The ring labeled B is a nucleobase. $R^{n3}$ is —OH or a phosphoramidite. $R^{n5}$ is —OH or —ODMT.

A compound according to any preceding paragraph, wherein $R^8$ is selected from:

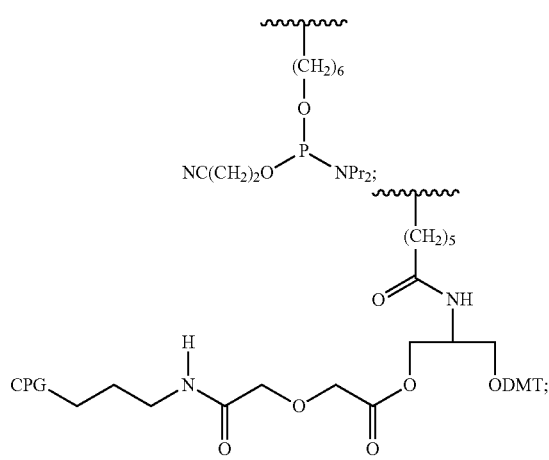

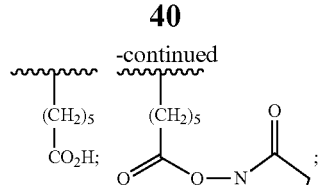

-continued

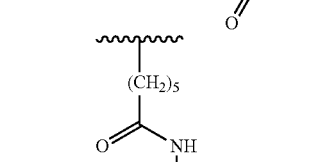

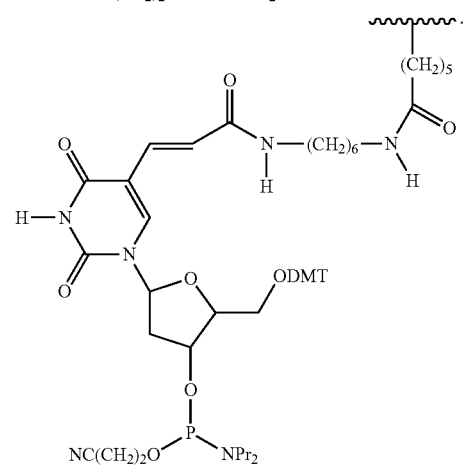

A method for detecting a nucleic acid target sequence, the method comprising:
(a) contacting the target sequence with a detector nucleic acid; comprising a single-stranded target binding sequence, the detector nucleic acid having linked thereto,
  i) a fluorophore; and
  ii) a compound according to any preceding paragraph, wherein $R^8$ comprises a linkage site covalently bound (directly or through a linker) to the detector nucleic acid;
wherein the detector nucleic acid is in a conformation allowing donor-acceptor energy transfer between the fluorophore and the compound when the fluorophore is excited;
(b) hybridizing the target binding sequence to the target sequence, thereby altering the conformation of the detector nucleic acid, causing a change in a fluorescence parameter; and
(c) detecting the change in the fluorescence parameter, thereby detecting the nucleic acid target sequence.

A method of ascertaining whether a first nucleic acid and a second nucleic acid hybridize, the first nucleic acid comprising a compound according to any preceding paragraph, wherein $R^8$ comprises a linkage site covalently bound (directly or through a linker) to the first nucleic acid, the method comprising:
(a) contacting the first nucleic acid with the second nucleic acid; and (b) detecting an alteration in a fluorescent property of a member selected from the first nucleic acid, the second nucleic acid and a combination thereof, thereby ascertaining whether the hybridization occurs.

A method of monitoring a nucleic acid amplification reaction, the method comprising:
(a) preparing an amplification reaction mixture comprising a detector nucleic acid having linked thereto,
 i) a fluorophore; and
 ii) a compound according to any preceding paragraph, wherein $R^8$ comprises a linkage site covalently bound (directly or through a linker) to the detector nucleic acid;
(b) subjecting the amplification reaction mixture to amplification conditions;
(c) monitoring the reaction mixture for a fluorescent signal from the detector nucleic acid to obtain an assay result; and
(d) employing the assay result to monitor the nucleic acid amplification reaction.

A method of detecting amplification of a target sequence, the method comprising:
(a) hybridizing a sample nucleic acid comprising the target sequence with PCR primers that flank the target sequence;
(b) extending the hybridized primers with a polymerase to produce the PCR product, and separating the two strands of the PCR product to make accessible the sense and antisense strands of the target sequence;
(c) hybridizing a detector nucleic acid to the sense or antisense strand of the target sequence in the PCR product, wherein the detector nucleic acid includes:
 i) a single stranded target binding sequence that is complementary to at least a portion of the sense or antisense strand of the target sequence in the PCR product, and hybridizes to a region between the PCR primers;
 ii) a fluorophore; and
 iii) a compound according to any preceding paragraph, wherein $R^8$ comprises a linkage site covalently bound (directly or through a linker) to the detector nucleic acid;
 wherein prior to its hybridization to the target sequence, the detector nucleic acid is in a conformation allowing donor-acceptor energy transfer between the fluorophore and the compound when the fluorophore is excited;
 thereby altering the conformation of the detector nucleic acid, causing a change in a fluorescence parameter; and
(d) measuring the change in the fluorescence parameter to detect the target sequence and its amplification.

The materials and methods of the present invention are further illustrated by the examples which follow. These examples are offered to illustrate, but not to limit the claimed invention.

EXAMPLES

Example 1: Synthesis of Exemplary Compounds of the Invention

The synthesis of various exemplary compounds of the invention is outlined in FIG. 2.

Hydroxytetramethyljulolidine 2 was prepared via the hydroxyaniline 1 without need for chromatography in about 50% overall yield for the two steps (Dyes and Pigments 2003, 59, 63). Scale up afforded 95 g of 2 with relative ease. Test reaction of 2 with Fast Black K (FBK) salt generated the deep blue dye 3. Conversion of 2 to the $C_6$-hydroxyl compound 4 was effected using excess chlorohexanol and potassium carbonate in DMF under anhydrous conditions. The literature method for alkylation using sodium hydride in dry DMF was avoided to minimize difficulties during large-scale production. Addition of a methanol-water solution of Fast Black K salt to a methanol solution of the 4 afforded azo dye alcohol 5, which was converted to the amidite 6. Scale up gave about 13 g of the amidite. The amidite was used to make 5'-labeled poly T oligos, which were dual HPLC purified and then used to determine extinction coefficients for the dye.

Reaction of bromohexanoic acid with 2 as above did not afford the desired compound 7. Bromohexanoic acid was converted to its methyl ester 8, which was then coupled to 2 to give the respective $C_6$— ester compound 9 that was not isolated. Cleavage of the methyl ester using 2 M aqueous sulfuric acid in THF gave the $C_6$-acid compound 7. Coupling to FBK salt gave the acid-azo dye 10 that was used to prepare the DMT protected serinol derivative 11. This was converted sequentially to the glycolate 12 and then the CPG 13. The CPG was used to make 3'-labeled poly T oligos, which were dual HPLC purified, and then were used to determine extinction coefficients for the dye. As with the 5'-labeled oligonucleotides, no significant traces of dye decomposition or byproducts were seen by HPLC in the crude oligonucleotide samples after deprotection under basic conditions. The acid azo dye 10 was converted to the active ester 14.

Example 2: BHQ2, BBQ and Cosmic Quencher Performance Comparison

Introduction

The performance was evaluated of a Cosmic Quencher (shown below) to quench dyes emitting light at longer wavelengths. Specifically, the quencher's ability to extinguish signal from the fluorophores Quasar 670 and Quasar 705 was examined. As references, the performance of BHQ2 and BlackBerry Quencher (BBQ-650®; Berry & Associates, Inc.; described in U.S. Pat. No. 7,879,986) was also examined when partnered with these same fluorophores. TaqMan probes containing each of these quenchers were evaluated by both real-time PCR and nuclease digestion assays.

Scheme. Quencher Moieties.

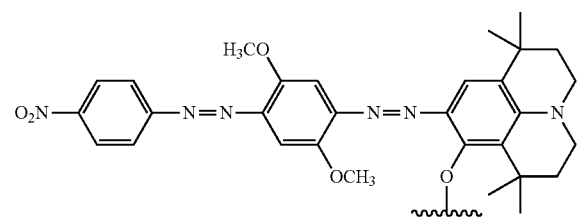

Cosmic Quencher

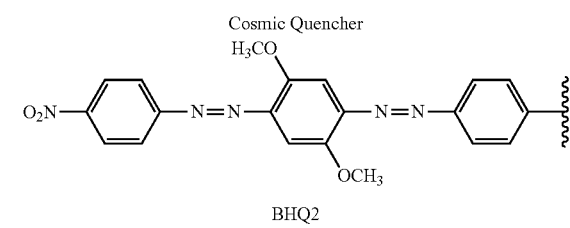

BHQ2

-continued

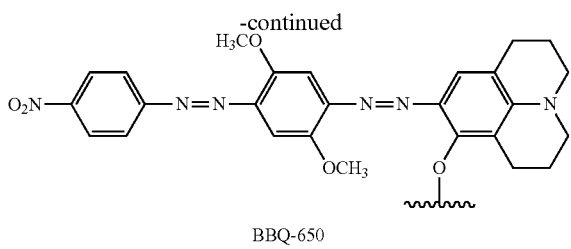

BBQ-650

Methods

A model TaqMan assay was utilized for all comparisons in this study, and designed to detect the the human gene for cholinergic receptor, muscarinic 3 (Gene ID CHRM3, accession number nm_000740). The probe sequence is 5'-[Fluorophore]-TCCTTTGGGCTCCTGCCATCT-[Quencher]-3' and signals the amplification product of the PCR primers 5'-TTGGGTCATCTCCTTTG-3' and 5'-GCACAGT-TCTCTTTCCA-3'. This probe sequence was synthesized with each of five different fluorophore quencher combinations: Quasar 670-Cosmic Quencher, Quasar 670-BHQ2, Quasar 670-BBQ, Quasar 705-Cosmic Quencher and Quasar 705-BHQ2. Each probe was partnered with the same primer set and their quenching efficiencies were evaluated with triplicate reactions of PCR amplification from 25 ng of human genomic DNA. The composition of each reaction is as follows:

| Component (Stock Concentration) | Volume | Final Concentration |
| --- | --- | --- |
| Nuclease-free water | 10.25 µL | N/A |
| Platinum Taq PCR Buffer (10X) | 5.00 µL | 1X |
| TaqMan Probe (10 µM) | 0.50 µL | 100 nM |
| MgCl$_2$ (50 mM) | 2.00 µL | 2.0 mM |
| dNTPs (2.5 mM each) | 4.00 µL | 200 µM each |
| Human genomic DNA (150 pg/µL) | 25.0 µL | 3.75 ng per reaction |
| Platinum Taq Polymerase (1 U/µL) | 0.25 µL | 1.25 units per reaction |
| Forward Primer (10 µM) | 1.50 µL | 300 nM |
| Reverse Primer (10 µM) | 1.50 µL | 300 nM |
| Total Volume: | 50.0 µL | |

The real-time PCR reactions were cycled on the RotorGene 6000 (Corbett Research), with Quasar 670 detected on the "Red" channel (625 nm source, 660 nm detector, gain=5) and Quasar 705 detected on the "Crimson" channel (680 nm source, 710 nm detector, gain=10). The 5 probes were then examined by a nuclease digestion assay in which 1.5 units of micrococcal nuclease are added to a 100 µL solution of nuclease buffer with probe at a concentration of 400 nM. The digestion is allowed to proceed for a 10 minute interval. Following that interval, the signal intensity is measured on a Tecan Safire fluorometer with the following settings:

| Settings | Quasar 670 | Quasar 705 |
| --- | --- | --- |
| Measurement mode: | fluorescence Top | fluorescence Top |
| Excitation wavelength: | 641 nm | 680 nm |
| Emission wavelength: | 676 nm | 715 nm |
| Excitation bandwidth: | 12 nm | 12 nm |
| Emission bandwidth: | 12 nm | 12 nm |
| Gain: | 150 | 150 |
| Number of flashes: | 20 | 20 |
| Lag time: | 0 µs | 0 µs |
| Integration time: | 20 µs | 20 µs |

Signal-to-noise values are calculated by dividing the fluorescence intensity of the probe in the reaction treated with nuclease by the intensity of the same probe in an untreated reaction, after first subtracting the signal of buffer blanks from each.

Real-Time PCR Results

Figure 3:
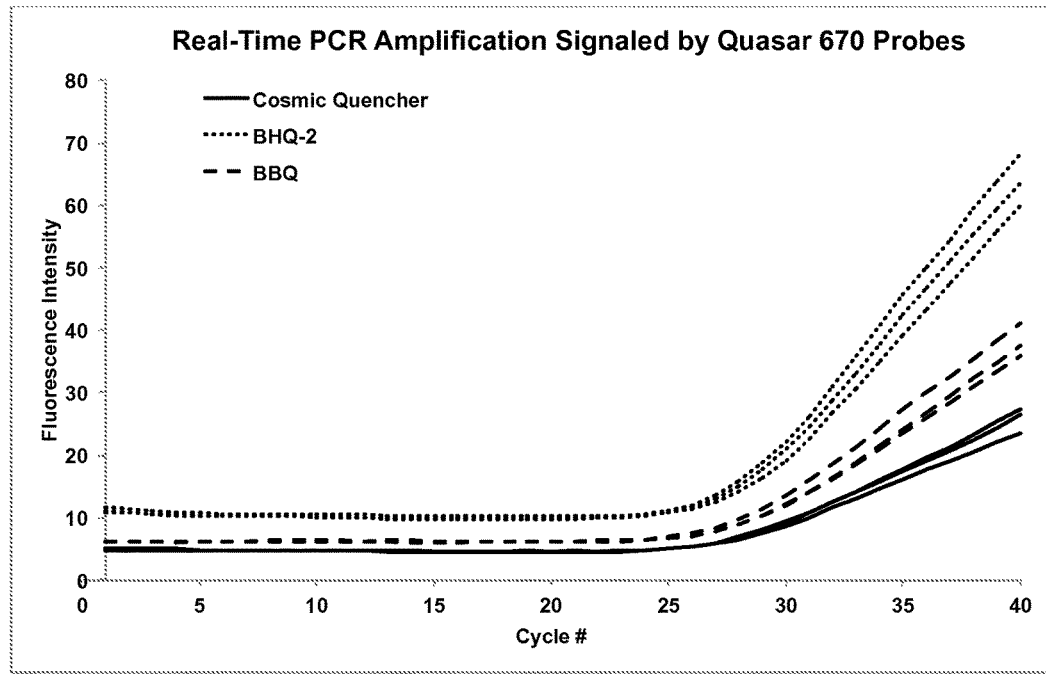
FIG. 3 shows the amplification traces for Quasar 670-Cosmic Quencher, Quasar 670-BHQ2, and Quasar 670-BBQ probes in a real-time PCR assay.
Figure 4:
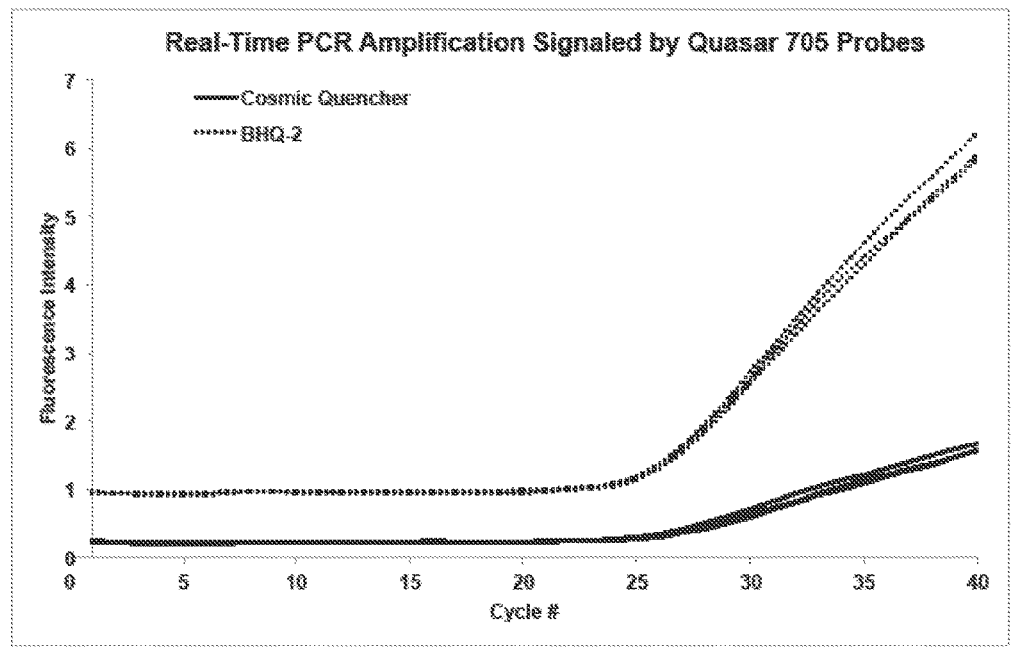
FIG. 4 shows the amplification traces for Quasar 705-Cosmic Quencher and Quasar 705-BHQ2 probes in a real-time PCR assay.

Within the Quasar 670 plots (FIG. 3), the solid amplification traces represent the Cosmic Quencher probe, the dashed traces represent the BlackBerry Quencher (BBQ) probe, and the dotted traces represent the BHQ2 probe. Within the Quasar 705 plots (FIG. 4), the solid traces denote the Cosmic Quencher probe while the dotted traces denote the BHQ2 probe. With either fluorophore, Cosmic Quencher demonstrates more efficient quenching than BHQ2 or BBQ, as evidenced by the baseline signal intensity before the onset of amplification.

Nuclease Digestion Results

The nuclease assay reveals that both fluorophores are quenched most efficiently by Cosmic Quencher, particularly with Quasar 705 which demonstrates ⅙ the background fluorescence than with BHQ2. Due to its superior quenching efficiency, Cosmic Quencher demonstrates the highest signal-to-noise ratio with Quasar 705 and the second highest ratio with Quasar 670.

Figure 5A:
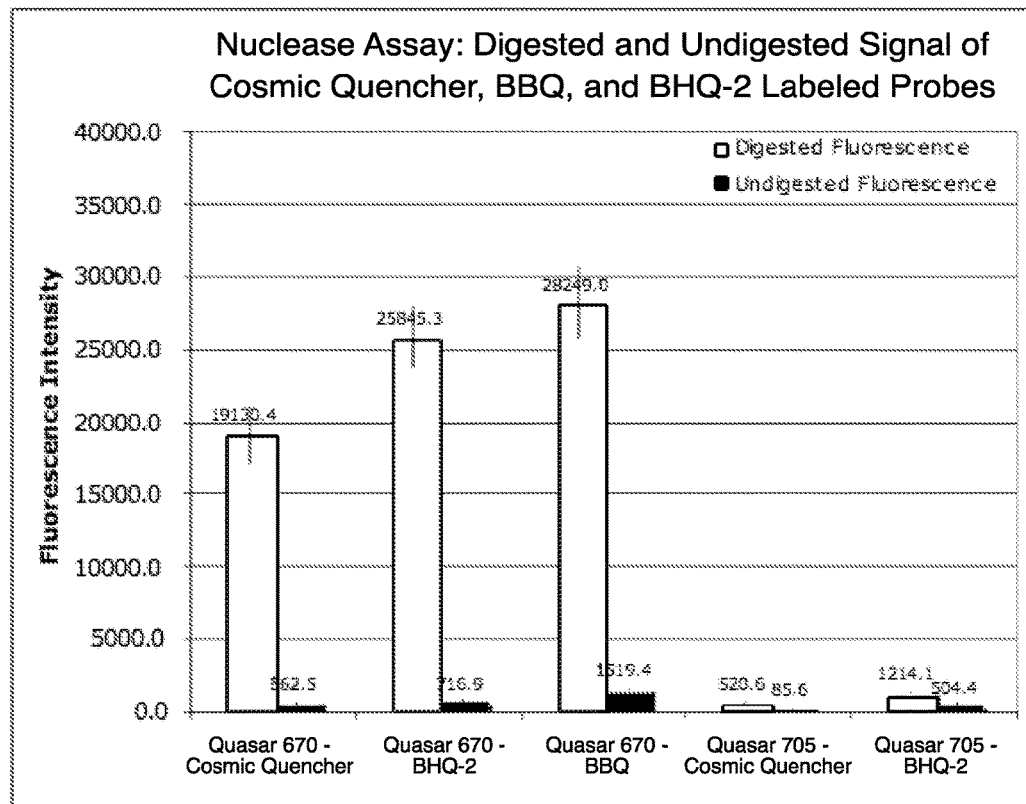
FIG. 5A-FIG. 5B.
Figure 5B:
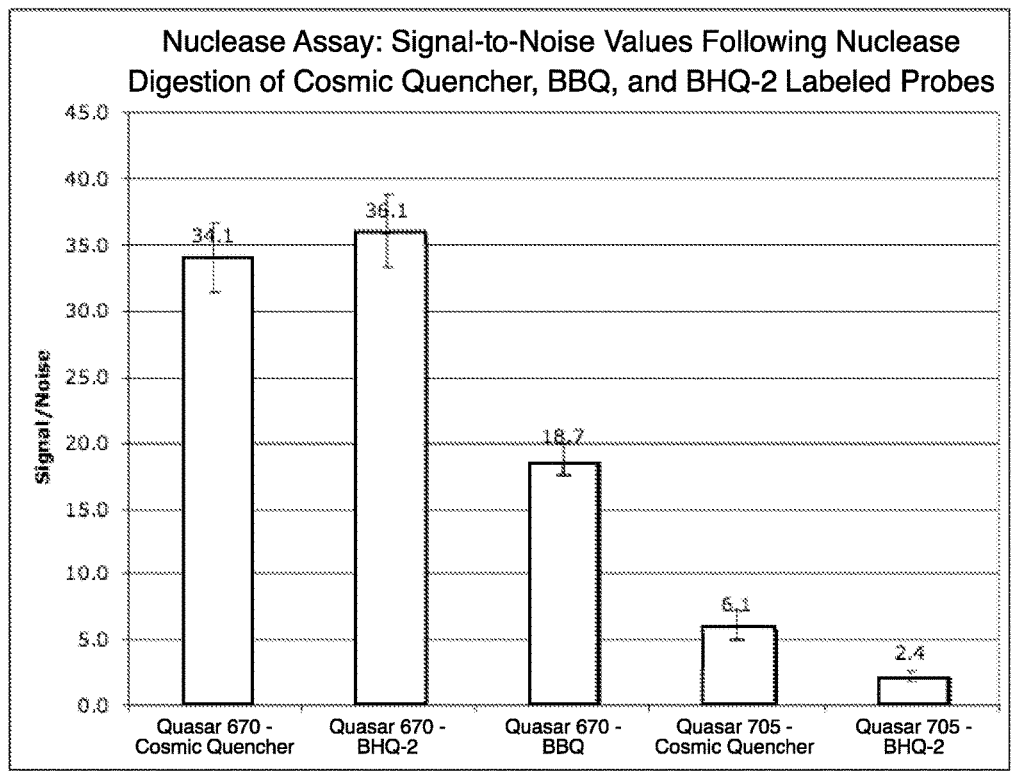

FIG. 5A shows the measured fluorescence intensity with and without digestion of the probes labeled with Quasar 670-Cosmic Quencher, Quasar 670-BHQ2, Quasar 670-BBQ, Quasar 705-Cosmic Quencher, and Quasar 705-BHQ2 in a nuclease assay. FIG. 5B shows the signal-to-noise ratios calculated from the digested and un-digested fluorescence of the probes labeled with Quasar 670-Cosmic Quencher, Quasar 670-BHQ2, Quasar 670-BBQ, Quasar 705-Cosmic Quencher, and Quasar 705-BHQ2 in a nuclease digestion assay.

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A compound having a structure according to Formula I or II:

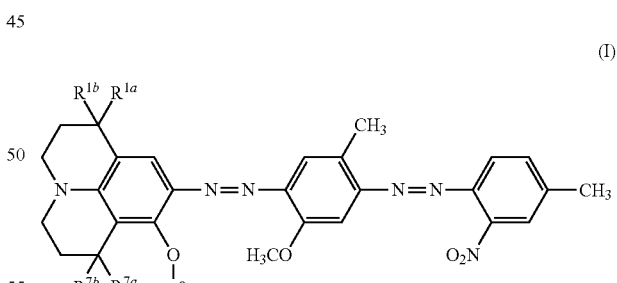

(I)

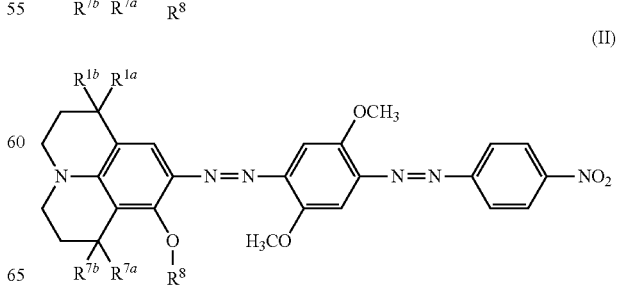

(II)

wherein

R$^{1a}$, R$^{1b}$, R$^{7a}$, and R$^{7b}$ are independently selected from substituted or unsubstituted alkyl, substituted or unsubstituted cycloalkyl, substituted or unsubstituted heteroalkyl, and substituted or unsubstituted heterocycloalkyl;

and R$^{1a}$ and R$^{1b}$, together with the carbon atom to which they are attached, are optionally joined to form a ring which is a member selected from substituted or unsubstituted C$_3$-C$_7$ cycloalkyl and substituted or unsubstituted 3- to 7-membered heterocycloalkyl;

and R$^{7a}$, and R$^{7b}$, together with the carbon atom to which they are attached, are optionally joined to form a ring which is a member selected from substituted or unsubstituted C$_3$-C$_7$ cycloalkyl and substituted or unsubstituted 3- to 7-membered heterocycloalkyl; and R$^8$ is selected from H,

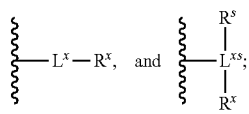

wherein L$^x$ is selected from a bond, substituted or unsubstituted alkyl, substituted or unsubstituted cycloalkyl, substituted or unsubstituted heteroalkyl, and substituted or unsubstituted heterocycloalkyl;

L$^{xs}$ is selected from substituted or unsubstituted alkyl, substituted or unsubstituted cycloalkyl, substituted or unsubstituted heteroalkyl, and substituted or unsubstituted heterocycloalkyl;

R$^s$ is selected from a protected or unprotected reactive functional group, a linkage site, and a solid support; and R$^x$ is selected from a protected or unprotected reactive functional group and a linkage site;

wherein each linkage site is covalently bound to a member independently selected from a nucleoside, a linker to a nucleoside, a nucleotide, a linker to a nucleotide, an oligonucleotide, a linker to an oligonucleotide, a nucleic acid, a linker to a nucleic acid, a carrier molecule, a linker to a carrier molecule, a solid support, and a linker to a solid support.

2. The compound according to claim 1, wherein R$^{1a}$ and R$^{1b}$ are independently selected from unsubstituted C$_1$, C$_2$, C$_3$, C$_4$, C$_5$, and C$_6$ alkyl.

3. The compound according to claim 2, wherein R$^{1a}$ and R$^{1b}$ are each methyl.

4. The compound according to claim 1, wherein R$^{7a}$ and R$^{7b}$ are independently selected from unsubstituted C$_1$, C$_2$, C$_3$, C$_4$, C$_5$, and C$_6$ alkyl.

5. The compound according to claim 4, wherein R$^{7a}$ and R$^{1b}$ are each methyl.

6. The compound according to claim 1, wherein R$^{1a}$, R$^{1b}$, R$^{7a}$, and R$^{7b}$ are independently selected from unsubstituted C$_1$, C$_2$, C$_3$, C$_4$, C$_5$, and C$_6$ alkyl.

7. The compound according to claim 6, wherein R$^{1a}$, R$^{1b}$, R$^{7a}$, and R$^{7b}$ are each methyl.

8. The compound according to claim 1, wherein L$^{xs}$ is selected from unsubstituted C$_1$, C$_2$, C$_3$, C$_4$, C$_5$, C$_6$, C$_7$, C$_8$, C$_9$, and C$_{10}$ alkyl.

9. The compound according to claim 1, wherein L$^{xs}$ is substituted heteroalkyl.

10. The compound according to claim 1, wherein R$^x$ is selected from a phosphoramidite, —OH, -ODMT, —COOH, an active ester, and —NH$_2$.

11. The compound according to claim 1, wherein R$^s$ is selected from —OH, —ODMT, and a linkage site covalently bound to a linker to a solid support.

12. The compound according to claim 11, wherein R$^x$ is selected from a phosphoramidite, —OH, -ODMT, —COOH, an active ester, and —NH$_2$.

13. The compound according to claim 1, wherein R$^x$ is a linkage site covalently bound to a linker to a nucleoside, wherein said nucleoside has the structure:

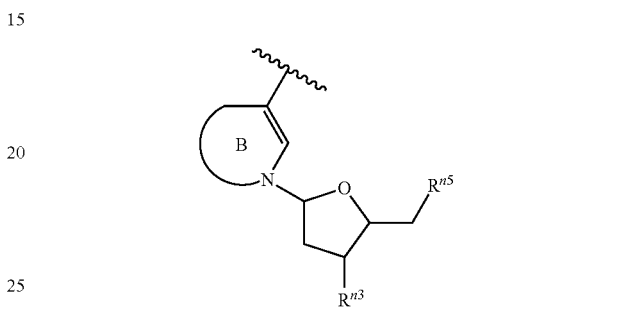

wherein the ring labeled B is a nucleobase;

R$^{n3}$ is OH or a phosphoramidite; and

R$^{n5}$ is OH or -ODMT.

14. The compound according to claim 1, wherein R$^8$ is selected from:

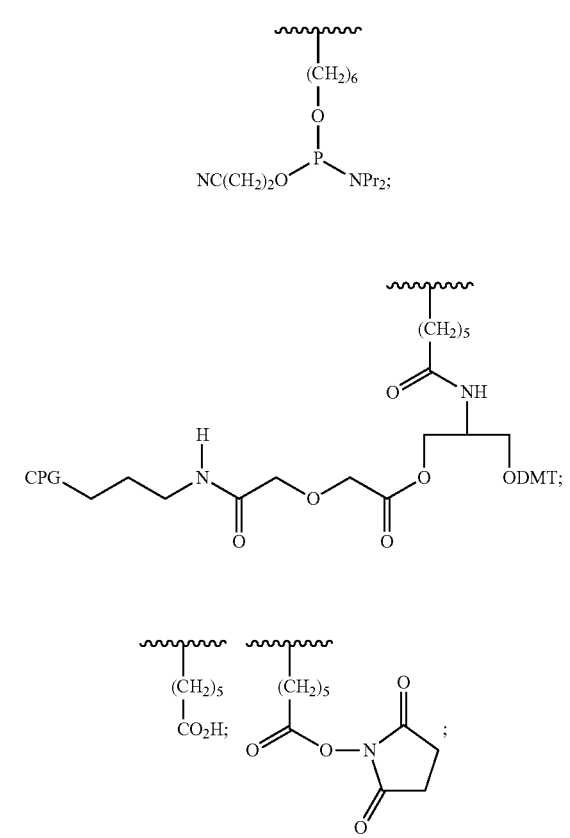

-continued

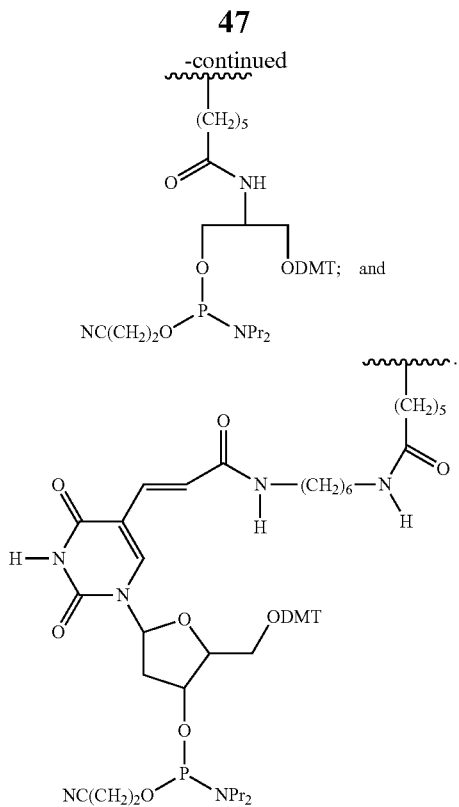

15. A method for detecting a nucleic acid target sequence, said method comprising:
(a) contacting said target sequence with a detector nucleic acid; comprising a single-stranded target binding sequence, said detector nucleic acid having linked thereto,
  i) a fluorophore; and
  ii) a compound according to claim 1, wherein $R^8$ comprises a linkage site covalently bound (directly or through a linker) to said detector nucleic acid;
wherein said detector nucleic acid is in a conformation allowing donor-acceptor energy transfer between said fluorophore and said compound when said fluorophore is excited;
(b) hybridizing said target binding sequence to said target sequence, thereby altering said conformation of said detector nucleic acid, causing a change in a fluorescence parameter; and
(c) detecting said change in said fluorescence parameter, thereby detecting said nucleic acid target sequence.

16. A method of ascertaining whether a first nucleic acid and a second nucleic acid hybridize, said first nucleic acid comprising a compound according to claim 1, wherein $R^8$ comprises a linkage site covalently bound (directly or through a linker) to said first nucleic acid, said method comprising:
(a) contacting said first nucleic acid with said second nucleic acid; and
(b) detecting an alteration in a fluorescent property of a member selected from said first nucleic acid, said second nucleic acid and a combination thereof, thereby ascertaining whether said hybridization occurs.

17. A method of monitoring a nucleic acid amplification reaction, said method comprising:
(a) preparing an amplification reaction mixture comprising a detector nucleic acid having linked thereto,
  i) a fluorophore; and
  ii) a compound according to claim 1, wherein $R^8$ comprises a linkage site covalently bound (directly or through a linker) to said detector nucleic acid;
(b) subjecting the amplification reaction mixture to amplification conditions;
(c) monitoring the reaction mixture for a fluorescent signal from the detector nucleic acid to obtain an assay result; and
(d) employing the assay result to monitor the nucleic acid amplification reaction.

18. A method of detecting amplification of a target sequence, said method comprising:
(a) hybridizing a sample nucleic acid comprising the target sequence with PCR primers that flank the target sequence;
(b) extending the hybridized primers with a polymerase to produce the PCR product, and separating the two strands of the PCR product to make accessible the sense and antisense strands of the target sequence;
(c) hybridizing a detector nucleic acid to the sense or antisense strand of the target sequence in the PCR product, wherein the detector nucleic acid comprises:
  i) a single stranded target binding sequence that is complementary to at least a portion of the sense or antisense strand of the target sequence in the PCR product, and hybridizes to a region between the PCR primers;
  ii) a fluorophore; and
  iii) a compound according to claim 1, wherein $R^8$ comprises a linkage site covalently bound (directly or through a linker) to said detector nucleic acid;
wherein prior to its hybridization to the target sequence, the detector nucleic acid is in a conformation allowing donor-acceptor energy transfer between the fluorophore and the compound when the fluorophore is excited;
thereby altering the conformation of the detector nucleic acid, causing a change in a fluorescence parameter; and
(d) measuring the change in the fluorescence parameter to detect the target sequence and its amplification.

19. A compound having a structure according to Formula I:

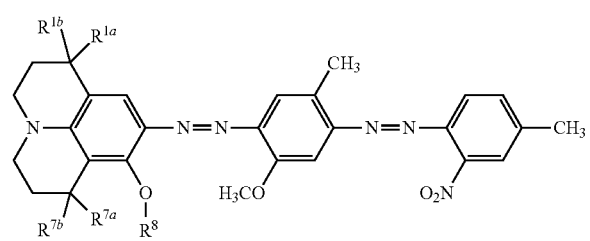

wherein
$R^{1a}$, $R^{1b}$, $R^{7a}$, $R^{7b}$ are independently selected from H, substituted or unsubstituted alkyl, substituted or unsubstituted cycloalkyl, substituted or unsubstituted heteroalkyl, and substituted or unsubstituted heterocycloalkyl;
and $R^{1a}$ and $R^{1b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl;

and $R^{7a}$, and $R^{7b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl;

wherein at least one of $R^{1a}$, $R^{1b}$, $R^{7a}$, and $R^{7b}$ is not H; and $R^8$ is selected from H,

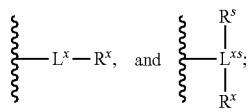

wherein $L^x$ is selected from a bond, substituted or unsubstituted alkyl, substituted or unsubstituted cycloalkyl, substituted or unsubstituted heteroalkyl, and substituted or unsubstituted heterocycloalkyl;

$L^{xs}$ is selected from substituted or unsubstituted alkyl, substituted or unsubstituted cycloalkyl, substituted or unsubstituted heteroalkyl, and substituted or unsubstituted heterocycloalkyl;

$R^s$ is selected from a protected or unprotected reactive functional group, a linkage site, and a solid support; and $R^x$ is selected from a protected or unprotected reactive functional group and a linkage site;

wherein each linkage site is covalently bound to a member independently selected from a nucleoside, a linker to a nucleoside, a nucleotide, a linker to a nucleotide, an oligonucleotide, a linker to an oligonucleotide, a nucleic acid, a linker to a nucleic acid, a carrier molecule, a linker to a carrier molecule, a solid support, and a linker to a solid support.

20. The compound according to claim 19, wherein $R^{1a}$ and $R^{1b}$ are independently selected from unsubstituted $C_1$, $C_2$, $C_3$, $C_4$, $C_5$, and $C_6$ alkyl.

21. The compound according to claim 20, wherein $R^{1a}$ and $R^{1b}$ are each methyl.

22. The compound according to claim 20, wherein $R^{7a}$ and $R^{7b}$ are each H.

23. The compound according to claim 19, wherein $R^{7a}$ and $R^{7b}$ are independently selected from unsubstituted $C_1$, $C_2$, $C_3$, $C_4$, $C_5$, and $C_6$ alkyl.

24. The compound according to claim 23, wherein $R^{7a}$ and $R^{7b}$ are each methyl.

25. The compound according to claim 23, wherein $R^{1a}$ and $R^{1b}$ are each H.

26. The compound according to claim 19, wherein $R^{1a}$, $R^{1b}$, $R^{7a}$, and $R^{7b}$ are independently selected from unsubstituted $C_1$, $C_2$, $C_3$, $C_4$, $C_5$, and $C_6$ alkyl.

27. The compound according to claim 26, wherein $R^{1a}$, $R^{1b}$, $R^{7a}$, and $R^{7b}$ are each methyl.

28. A compound according to Formula II;

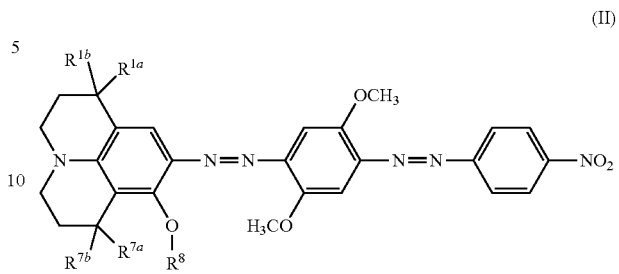

wherein
$R^{1a}$, $R^{1b}$, $R^{7a}$, and $R^{7b}$ are independently selected from substituted or unsubstituted alkyl, substituted or unsubstituted cycloalkyl, substituted or unsubstituted heteroalkyl, and substituted or unsubstituted heterocycloalkyl;

and $R^{1a}$ and $R^{1b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl;

and $R^{7a}$, and $R^{7b}$, together with the carbon atom to which they are attached, are optionally joined to form a ring which is a member selected from substituted or unsubstituted $C_3$-$C_7$ cycloalkyl and substituted or unsubstituted 3- to 7-membered heterocycloalkyl;

wherein a member selected from:
(i) $R^{1a}$ and $R^{1b}$;
(ii) $R^{7a}$ and $R^{7b}$; and
(iii) a combination thereof is independently selected from unsubstituted $C_1$, $C_2$, $C_3$, $C_4$, $C_5$, and $C_6$ alkyl; and $R^8$ is selected from H,

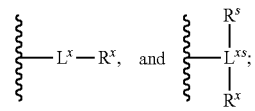

wherein $L^x$ is selected from a bond, substituted or unsubstituted alkyl, substituted or unsubstituted cycloalkyl, substituted or unsubstituted heteroalkyl, and substituted or unsubstituted heterocycloalkyl;

$L^{xs}$ is selected from substituted or unsubstituted alkyl, substituted or unsubstituted cycloalkyl, substituted or unsubstituted heteroalkyl, and substituted or unsubstituted heterocycloalkyl;

$R^s$ is selected from a protected or unprotected reactive functional group, a linkage site, and a solid support; and $R^x$ is selected from a protected or unprotected reactive functional group and a linkage site;

wherein each linkage site is covalently bound to a member independently selected from a nucleoside, a linker to a nucleoside, a nucleotide, a linker to a nucleotide, an oligonucleotide, a linker to an oligonucleotide, a nucleic acid, a linker to a nucleic acid, a carrier molecule, a linker to a carrier molecule, a solid support, and a linker to a solid support.

29. The compound according to claim 28, wherein $R^{1a}$ and $R^{1b}$ are each methyl.

30. The compound according to claim 28, wherein $R^{7a}$ and $R^{7b}$ are each methyl.

31. The compound according to claim 19, wherein $R^{1a}$, $R^{1b}$, $R^{7a}$, and $R^{7b}$ are independently selected from unsubstituted $C_1$, $C_2$, $C_3$, $C_4$, $C_5$, and $C_6$ alkyl.

32. The compound according to claim 28, wherein $R^{1a}$, $R^{1b}$, $R^{7a}$, and $R^{7b}$ are each methyl.

\* \* \* \* \*